US009343683B2

(12) United States Patent
Becker et al.

(10) Patent No.: US 9,343,683 B2
(45) Date of Patent: May 17, 2016

(54) COMPOUNDS FOR ELECTRONIC DEVICES

(75) Inventors: Heinrich Becker, Hofheim (DE);
Jochen Schwaiger, Frankfurt am Main
(DE); Hubert Spreitzer, Viernheim
(DE); Frank Voges, Bad Duerkheim
(DE); Holger Heil, Frankfurt am Main
(DE)

(73) Assignee: Merck Patent GmbH, Darmstadt (DE)

( * ) Notice: Subject to any disclaimer, the term of this patent is extended or adjusted under 35 U.S.C. 154(b) by 784 days.

(21) Appl. No.: 13/637,402

(22) PCT Filed: Feb. 28, 2011

(86) PCT No.: PCT/EP2011/000966
§ 371 (c)(1),
(2), (4) Date: Sep. 26, 2012

(87) PCT Pub. No.: WO2011/116869
PCT Pub. Date: Sep. 29, 2011

(65) Prior Publication Data
US 2013/0015403 A1   Jan. 17, 2013

(30) Foreign Application Priority Data

Mar. 26, 2010   (DE) .......................... 10 2010 013 068

(51) Int. Cl.
| | | |
|---|---|---|
| *H01L 51/54* | (2006.01) | |
| *C09K 11/06* | (2006.01) | |
| *H01L 51/00* | (2006.01) | |
| *C07C 211/61* | (2006.01) | |
| *H01L 51/50* | (2006.01) | |

(52) U.S. Cl.
CPC ............ *H01L 51/006* (2013.01); *C07C 211/61* (2013.01); *H01L 51/0059* (2013.01); *C07C 2103/94* (2013.01); *H01L 51/5048* (2013.01); *Y02E 10/549* (2013.01)

(58) Field of Classification Search
None
See application file for complete search history.

(56) References Cited

U.S. PATENT DOCUMENTS

| | | |
|---|---|---|
| 6,747,287 B1 | 6/2004 | Toguchi et al. |
| 2006/0049397 A1 | 3/2006 | Pfeiffer et al. |
| 2006/0210830 A1* | 9/2006 | Funahashi ............. C07C 211/61 428/690 |
| 2007/0003785 A1 | 1/2007 | Slusarek et al. |
| 2007/0077450 A1 | 4/2007 | Yen et al. |
| 2008/0102312 A1 | 5/2008 | Parham et al. |
| 2008/0191617 A1 | 8/2008 | Chae et al. |
| 2009/0167161 A1 | 7/2009 | Yabunouchi et al. |
| 2011/0198578 A1 | 8/2011 | Heuser et al. |

FOREIGN PATENT DOCUMENTS

| | | |
|---|---|---|
| CN | 1412864 A | 4/2003 |
| CN | 1734806 A | 2/2006 |
| EP | 1624500 A1 | 2/2006 |
| JP | 2004087395 A | 3/2004 |
| JP | 2004095428 A | 3/2004 |
| JP | 2005158561 A | 6/2005 |
| JP | 2007534814 A | 11/2007 |
| JP | 2012505535 A | 3/2012 |
| TW | 200932870 A | 8/2009 |
| WO | WO-2009/089472 A2 | 7/2009 |
| WO | WO-2009084268 A1 | 7/2009 |
| WO | WO-2010004887 A1 | 1/2010 |

OTHER PUBLICATIONS

Shen, Jiun Yi, et al., "High Tg blue emitting materials for electroluminescent devices", Journal of Materials Chemistry, 2005, 15, 2455-2463.
International Search Report for PCT/EP2011/0000966 mailed Apr. 6, 2011.

* cited by examiner

*Primary Examiner* — Andrew K Bohaty
(74) *Attorney, Agent, or Firm* — Drinker Biddle & Reath LLP

(57) ABSTRACT

The present invention relates to compounds having a spiro-bifluorene skeleton of the formula (I) for use as functional materials in electronic devices, in particular for use in the charge-transport layer and/or emission layer of organic electroluminescent devices. The invention furthermore relates to a process for the preparation of the compounds according to the invention and to mixtures comprising the compounds according to the invention. The invention furthermore relates to the use of the compounds of the formula (I) in electronic devices and to electronic devices comprising the compounds of the formula (I).

16 Claims, No Drawings

COMPOUNDS FOR ELECTRONIC DEVICES

RELATED APPLICATIONS

This application is a national stage application (under 35 U.S.C. §371) of PCT/EP2011/000966, filed Feb. 28, 2011, which claims benefit of German Patent Application No. 10 2010 013 068.0, filed Mar. 26, 2010.

The present invention relates to compounds of the formula (I) having a spirobifluorene skeleton which are suitable for use as functional materials in electronic devices, in particular for use in the charge-transport layer and/or emission layer of organic electroluminescent devices. The invention furthermore relates to a process for the preparation of the compounds according to the invention and to mixtures comprising the compounds according to the invention. The invention furthermore relates to the use of the compounds in electronic devices and to electronic devices comprising the compounds.

In the area of functional materials for electronic devices, in particular in the area of functional materials for organic electroluminescent devices (OLEDs), there is a demand for novel compounds with which an improvement in the performance data of the devices can be achieved.

The general structure of organic electroluminescent devices is described, for example, in U.S. Pat. No. 4,539,507, U.S. Pat. No. 5,151,629, EP 0676461 and WO 98/27136.

There continues to be a need for improvement in the following points with respect to the performance data of these devices:
1. An increase in the power efficiency, in particular in fluorescent OLEDs, is desirable.
2. There is still a need for improvement in the operating lifetime of the devices, in particular in the case of blue emission.
3. A reduction in the operating voltage of the devices is desirable. This is of major importance, in particular, for mobile applications.

There continues to be a demand for materials having the properties mentioned below with respect to the functional materials for use in organic electroluminescent devices. This demand results, inter alia, from the correlation between material properties and performance data of the devices comprising the materials and from requirements made of the industrial processability of the materials.
1. Increased charge-carrier mobility (hole mobility). This preferably results in a reduction in the use voltage and thus an increase in the power efficiency in OLEDs. This property is likewise of crucial importance for use of the materials in organic solar cells in order to achieve high efficiency of the devices (low recombination). This property is likewise of crucial importance for use of the materials as organic semiconductors (for example in field-effect transistors), since this facilitates a high working frequency here, which is necessary for a large number of applications.
2. Stability of the materials to decomposition over a long period (preferably several days) at the evaporation temperature. This is of importance, in particular, in industrial processes, such as purification of the materials by sublimation and deposition of the materials from the gas phase during production of the devices.
3. Tendency to form amorphous films under suitable conditions, preferably during deposition from the gas phase and/or during printing from solution. This property usually correlates with a high glass transition temperature (Tg).
4. Adequate stability to environmental influences during industrial processing (for example oxygen and/or moisture in the air), which simplifies handling, for example during transfer of the materials. For use of the materials in printing processes, it is necessary, in particular, that the compounds in question are also stable to oxidation in solution over an adequate time.
5. Good synthetic accessibility in order to enable high purities and high yields. This enables a reduction in material costs and higher economic efficiency.

The use of functional materials having a spirobifluorene skeleton is known in the prior art. For example, EP 0676461 A2 discloses spirobifluorene derivatives, including compounds containing arylamino groups in the 2-, 2'-, 7- and 7'-position of the spirobifluorene skeleton, and the use thereof in organic electroluminescent devices.

These compounds are tetra(bisarylamino)spirobifluorenes, which have a relatively high molecular weight. However, there is a demand, in particular with respect to the above-mentioned requirement of long-term temperature stability, for novel functional materials which have a lower molecular weight than the spirobifluorenes disclosed in EP 0676461 A2, but still have good performance properties.

Furthermore, US 2009/167161 A1 discloses spirobifluorene derivatives which contain different diarylamine substituents in each of the 2,7-positions of the spirobifluorene skeleton, for use as functional materials in organic electroluminescent devices. These materials do not carry diarylamine substituents in the 2',7'-positions.

However, there continues to be a demand for novel functional materials which have good synthetic accessibility and can therefore be prepared economically, in particular with comparable or improved charge-carrier mobility.

Furthermore, JP 11-273863 A discloses spirobifluorene derivatives which have diarylamino substituents in each of the 2,7-positions, but carry no substituents or other substituents, for example aryl or heteroaryl substituents, in the 2',7'-positions. The compounds disclosed in JP 11-273863 A carry no further substituents on each of the aryl groups of the diarylamino radical.

However, there continues to be a demand for novel functional materials, in particular those which simultaneously have a high tendency to form amorphous films and good solubility in organic solvents, at the same time as comparable charge-carrier mobility.

In summary, the object of the present invention is to provide novel functional materials, in particular novel hole-transport and/or hole-injection materials for electronic devices, which have one or more of the advantageous properties mentioned above.

As described above, further improvements are desirable over the compounds disclosed in the prior art, in particular with respect to the points mentioned individually above.

Surprisingly, it has been found that 2,7-diarylamino-substituted spirobifluorene derivatives containing one or more alkyl substituents on the aryl groups of the diarylamino substituents are eminently suitable for use as functional materials in organic electroluminescent devices, preferably as hole-transport and/or hole-injection materials. In particular, these compounds are accompanied by improvements with respect to one or more of the above-mentioned properties.

The invention therefore provides compounds of the formula (I)

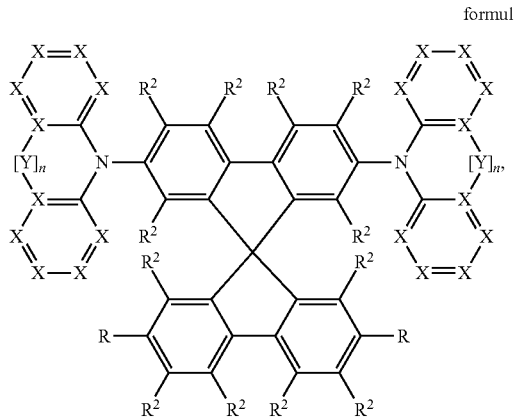

formula (I)

where the following applies to the symbols and indices used:

X is on each occurrence, identically or differently, CH or CR$^1$, where at least one group X is equal to CR$^1$, and where, if precisely one group X is equal to CR$^1$ on each of the two arylarnino groups, this cannot be in the meta-position to the bond to the nitrogen atom, and where furthermore X is equal to C if a group Y is bonded to the group X;

Y is on each occurrence, identically or differently, a single bond, O, S, C(R$^3$)$_2$ or NR$^3$;

R is on each occurrence, identically or differently, H, D, CHO, C(=O)R$^3$, P(=O)(R$^3$)$_2$, S(=O)R$^3$, S(=O)$_2$R$^3$, CN, NO$_2$, Si(R$^3$)$_3$, B(OR$^3$)$_2$, OSO$_2$R$^3$, OH, COOR$^3$, CON(R$^3$)$_2$, a straight-chain alkyl group having 1 to 4 C atoms or a branched or cyclic alkyl group having 3 to 40 C atoms or an alkenyl or alkynyl group having 2 to 40 C atoms, where one or more CH$_2$ groups in the alkyl, alkenyl and alkynyl groups may be replaced by Si(R$^3$)$_2$, C=O, C=S, C=Se, C=NR$^3$, P(=O)(R$^3$), SO, SO$_2$, NR$^3$, —O—, —S—, —COO— or —CONR$^3$— and the above-mentioned alkyl, alkenyl and alkynyl groups may be substituted by one or more groups R$^3$, or an aromatic or heteroaromatic ring system having 5 to 60 aromatic ring atoms, which may in each case be substituted by one or more non-aromatic radicals R$^3$, or an aryloxy or heteroaryloxy group having 5 to 60 aromatic ring atoms, which may be substituted by one or more non-aromatic radicals R$^3$, or a combination of these systems, where two radicals R may be linked to one another and may form an aliphatic or aromatic ring system;

R$^1$ is on each occurrence, identically or differently, a straight-chain alkyl group having 1 to 40 C atoms or a branched or cyclic alkyl group having 3 to 40 C atoms or an alkenyl or alkynyl group having 2 to 40 C atoms, where one or more CH$_2$ groups in the above-mentioned alkyl, alkenyl and alkynyl groups may be replaced by Si(R$^3$)$_2$, C=O, C=S, C=Se, C=NR$^3$, P(=O)(R$^3$), SO, SO$_2$, NR$^3$, —O—, —S—, —COO— or —CONR$^3$— and the above-mentioned alkyl, alkenyl and alkynyl groups may be substituted by one or more groups R$^3$, where two or more radicals R$^1$ may be linked to one another and may form a ring system;

R$^2$ is on each occurrence, identically or differently, H, D, F, Cl, Br, I, CHO, N(Ar)$_2$, N(R$^3$)$_2$, C(=O)R$^3$, P(=O)(R$^3$)$_2$, S(=O)R$^3$, S(=O)$_2$R$^3$, CR$^3$=C(R$^3$)$_2$, CN, NO$_2$, Si(R$^3$)$_3$, B(OR$^3$)$_2$, OSO$_2$R$^3$, OH, COOR$^3$, CON(R$^3$)2, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals R$^3$, where one or more non-adjacent CH$_2$ groups may be replaced by Si(R$^3$)$_2$, C=O, C=S, C=Se, C=NR$^3$, P(=O)(R$^3$), SO, SO$_2$, NR$^3$, —O—, —S—, —COO— or —CONR$^3$— and where one or more H atoms may be replaced by D, F, Cl, Br, I, CN or NO$_2$, or an aromatic or heteroaromatic ring system having 5 to 60 aromatic ring atoms, which may in each case be substituted by one or more non-aromatic radicals R$^3$, or an aryloxy or heteroaryloxy group having 5 to 60 aromatic ring atoms, which may be substituted by one or more non-aromatic radicals R$^3$, or a combination of these systems, where two or more radicals R$^2$ may be linked to one another and may form an aliphatic or aromatic ring system;

R$^3$ is on each occurrence, identically or differently, H, D, F, Cl, Br, I, CHO, N(R$^4$)$_2$, C(=O)R$^4$, P(=O)(R$^4$)$_2$, S(=O)R$^4$, S(=O)$_2$R$^4$, CR$^4$=C(R$^4$)$_2$, CN, NO$_2$, Si(R$^4$)$_3$, B(OR$^4$)$_2$, OSO$_2$R$^4$, OH, COOR$^4$, CON(R$^4$)$_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals R$^4$, where one or more non-adjacent CH$_2$ groups may be replaced by Si(R$^4$)$_2$, C=O, C=S, C=Se, C=NR$^4$, P(=O)(R$^4$), SO, SO$_2$, NR$^4$, —O—, —S—, —COO— or —CONR$^4$— and where one or more H atoms may be replaced by D, F, Cl, Br, I, CN or NO$_2$, or an aromatic or heteroaromatic ring system having 5 to 60 aromatic ring atoms, which may in each case be substituted by one or more non-aromatic radicals R$^4$, or an aryloxy or heteroaryloxy group having 5 to 60 aromatic ring atoms, which may be substituted by one or more non-aromatic radicals R$^4$, or a combination of these systems, where two or more radicals R$^3$ may be linked to one another and may form an aliphatic or aromatic ring system;

R$^4$ is, identically or differently on each occurrence, H, D, F or an aliphatic, aromatic and/or heteroaromatic organic radical having 1 to 20 C atoms, in which, in addition, one or more H atoms may be replaced by D or F; two or more identical or different substituents R$^4$ here may also be linked to one another and form an aliphatic or aromatic ring system;

Ar is on each occurrence, identically or differently, an aryl or heteroaryl group having 5 to 60 aromatic C atoms, which may be substituted by one or more radicals R$^3$;

n is on each occurrence, identically or differently, 0 or 1, where n=0 means that the group Y in question is not present;

and where the following compound is excluded

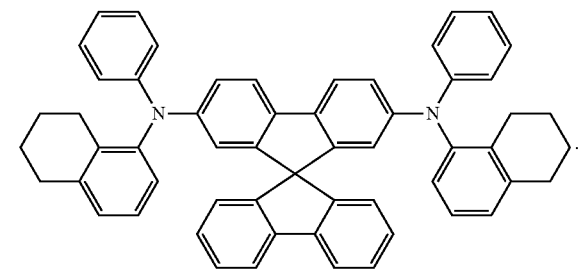 [SMILES: c1ccc(N(c2ccc3c(c2)C2(c4ccccc4-c4ccccc42)c2cc(N(c4ccccc4)c4cccc5c4CCCC5)ccc2-3)c2cccc3c2CCCC3)cc1]

The positions on the phenyl ring are designated in this application as meta-, para- and ortho-positions as usually used by the person skilled in the art in the area of organic chemistry. This is depicted below for clarification.

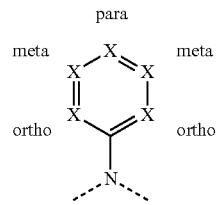

Furthermore, for the purposes of this invention, an aryl group contains 6 to 60 C atoms; for the purposes of this invention, a heteroaryl group contains 1 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (fused) aryl or heteroaryl group, for example naphthalene, anthracene, phenanthrene, quinoline, isoquinoline, carbazole, etc.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

For the purposes of this invention, an aromatic ring system contains 6 to 60 C atoms in the ring system. For the purposes of this invention, a heteroaromatic ring system contains 5 to 60 aromatic ring atoms, at least one of which is a heteroatom. The heteroatoms are preferably selected from N, O and/or S. For the purposes of this invention, an aromatic or heteroaromatic ring system is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an sp$^3$-hybridised C, Si, N or O atom, an sp$^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to mean aromatic ring systems for the purposes of this invention, and likewise systems in which two or more aryl groups are connected, for example, by a linear or cyclic alkyl, alkenyl or alkynyl group or by a silyl group. Systems in which two or more aryl or heteroaryl groups are linked to one another via one or more single bonds are also taken to be aromatic or heteroaromatic ring systems for the purposes of this invention.

An aromatic or heteroaromatic ring system having 5-60 aromatic ring atoms, which may also in each case be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or CH$_2$ groups may be substituted by the groups mentioned above under the definition of the radicals R$^2$ and R$^3$, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

It is preferred in accordance with the invention for 2 to 16 groups X per compound of the formula (I) to represent a group of the formula $CR^1$. It is particularly preferred in accordance with the invention for 3 to 12 groups X to represent a group of the formula $CR^1$. Very particularly preferably, 4 to 8 groups X represent a group of the formula $CR^1$.

It is furthermore preferred in accordance with the invention for 3 or more groups X per compound of the formula (I) to represent a group of the formula $CR^1$. It is particularly preferred in accordance with the invention for 4 or more groups X per compound of the formula (I) to represent a group of the formula $CR^1$.

In a further preferred embodiment, 1 to 4 groups X per aromatic six-membered ring represent a group of the formula $CR^1$, particularly preferably 1 to 3 groups X per aromatic six-membered ring represent a group of the formula $CR^1$ and very particularly preferably 1 or 2 groups X per aromatic six-membered ring represent a group of the formula $CR^1$. Especially preferably, precisely one group X per aromatic six-membered ring represents a group of the formula $CR^1$.

In a preferred embodiment of the invention, n=0, i.e. no groups Y are present.

A preferred embodiment of the compounds according to the invention is represented by the formula (II)

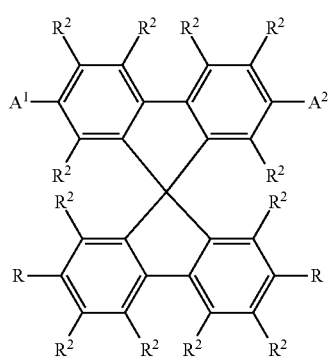

formula (II)

where the groups R and $R^2$ are as defined above and where furthermore
$A^1$, $A^2$ are selected on each occurrence, identically or differently, from a group of the formulae (1-1) to (1-55):

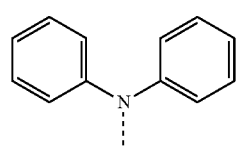

formula (1-1)

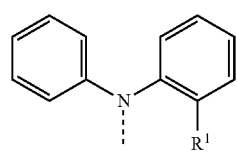

formula (1-2)

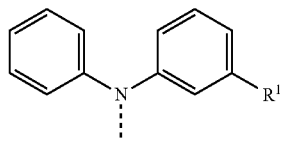

formula (1-3)

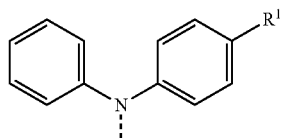

formula (1-4)

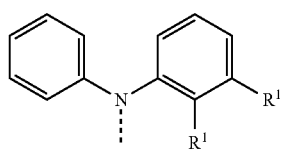

formula (1-5)

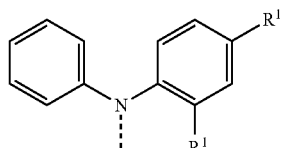

formula (1-6)

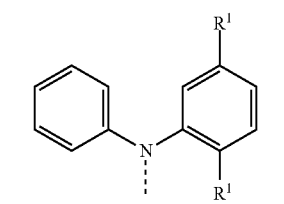

formula (1-7)

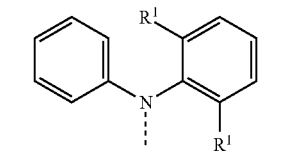

formula (1-8)

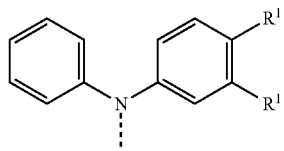

formula (1-9)

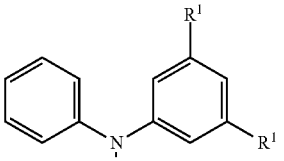

formula (1-10)

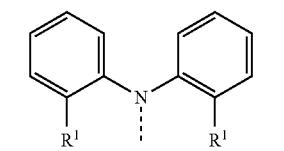

formula (1-11)

-continued
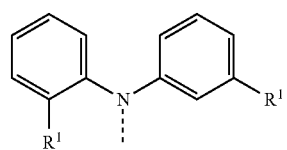
formula (1-12)
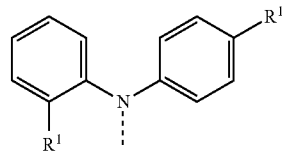
formula (1-13)
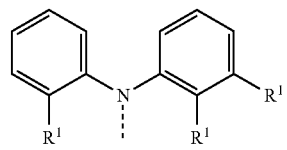
formula (1-14)
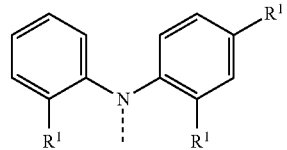
formula (1-15)
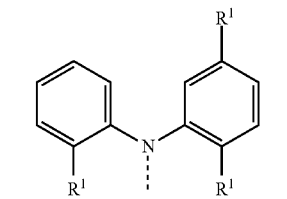
formula (1-16)
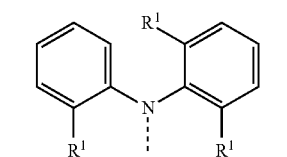
formula (1-17)
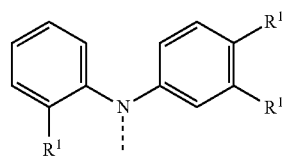
formula (1-18)
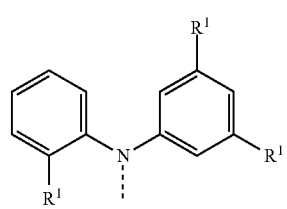
formula (1-19)
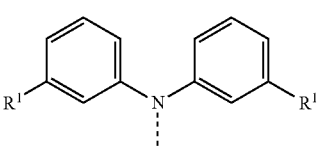
formula (1-20)
-continued
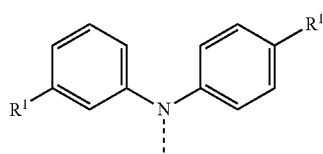
formula (1-21)
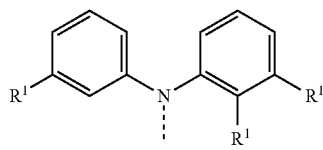
formula (1-22)
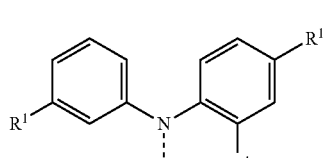
formula (1-23)
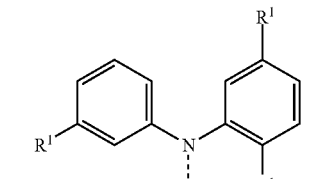
formula (1-24)
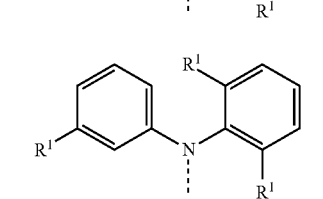
formula (1-25)
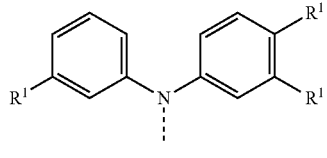
formula (1-26)
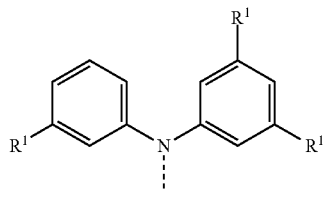
formula (1-27)
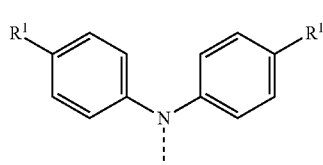
formula (1-28)
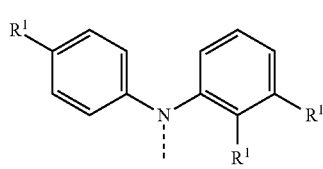
formula (1-29)

formula (1-30)
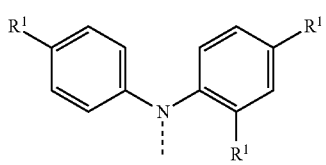
formula (1-31)
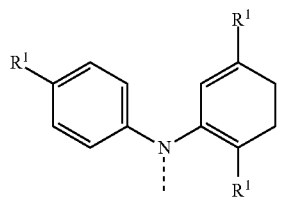
formula (1-32)
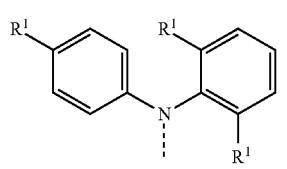
formula (1-33)
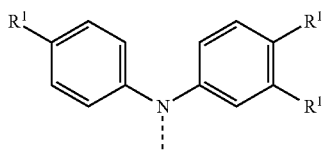
formula (1-34)
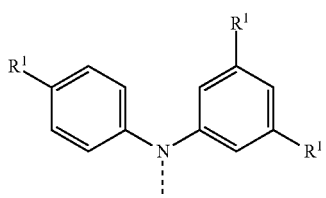
formula (1-35)
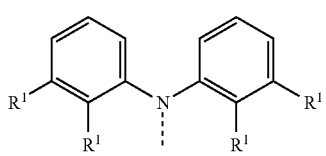
formula (1-36)
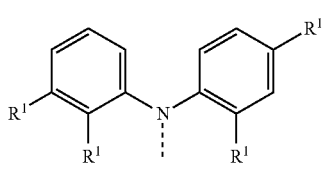
formula (1-37)
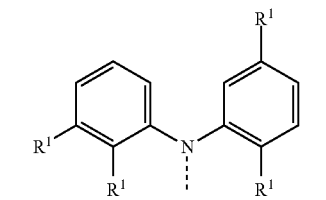
formula (1-38)
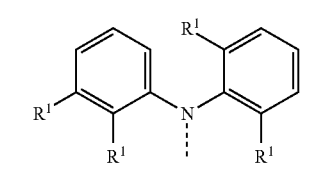
formula (1-39)
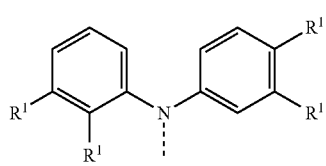
formula (1-40)
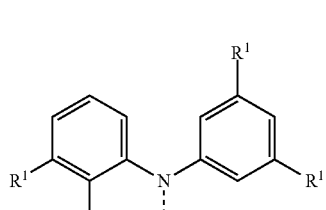
formula (1-41)
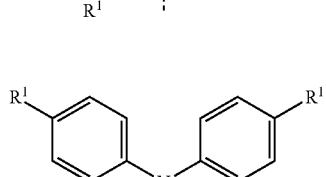
formula (1-42)
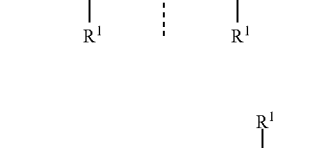
formula (1-43)
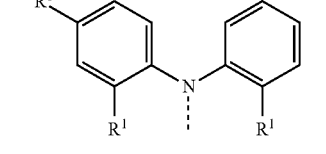
formula (1-44)
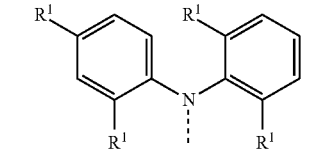
formula (1-45)
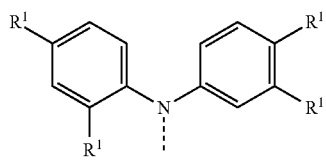
formula (1-46)
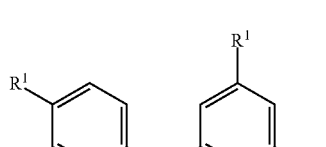
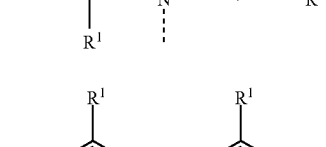

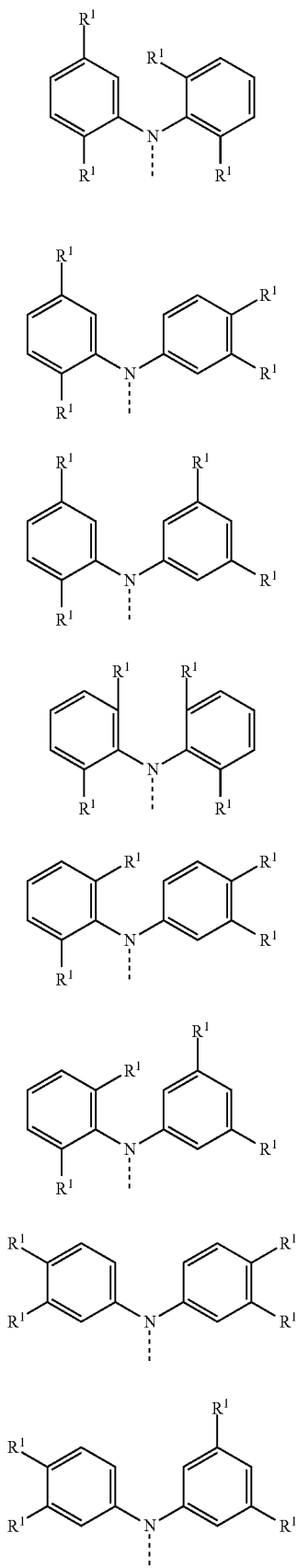

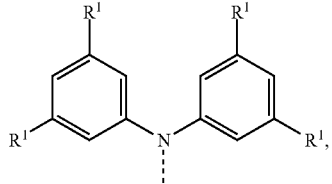

where the dashed line represents the bond from the group to the spirobifluorene unit and where $R^1$ is as defined above and where it is excluded for $A^1$ and $A^2$ both to represent a group of the formula (1-1) and where it is furthermore excluded for $A^1$ and $A^2$ both to represent a group of the formula (1-3).

Preferred embodiments of the groups $A^1$ and $A^2$ are groups of the formulae (1-4), (1-6), (1-9), (1-13), (1-15), (1-18), (1-21), (1-23), (1-26), (1-28), (1-29), (1-30), (1-31), (1-32), (1-33), (1-34), (1-36), (1-39), (1-41), (1-42), (1-43), (1-44), (1-45), (1-48), (1-51), (1-53) and (1-54).

In a preferred embodiment of the invention, $A^1$ and $A^2$ are identical.

In a preferred embodiment of the invention, R is on each occurrence, identically or differently, H, D, CHO, C(=O)$R^3$, P(=O)($R^3$)$_2$, S(=O)$R^3$, S(=O)$_2R^3$, CN, NO$_2$, Si($R^3$)$_3$, B(O$R^3$)$_2$, OSO$_2R^3$, OH, COO$R^3$, CON($R^3$)$_2$ or an alkenyl or alkynyl group having 2 to 40 C atoms, where one or more CH$_2$ groups in the alkenyl and alkynyl groups may be replaced by Si($R^3$)$_2$, C=O, C=S, C=Se, C=N$R^3$, P(=O)($R^3$), SO, SO$_2$, N$R^3$, —O—, —S—, —COO— or —CON$R^3$— and the above-mentioned alkenyl and alkynyl groups may be substituted by one or more groups $R^3$, or an aromatic or heteroaromatic ring system having 5 to 60 aromatic ring atoms, which may in each case be substituted by one or more non-aromatic radicals $R^3$, or an aryloxy or heteroaryloxy group having 5 to 60 aromatic ring atoms, which may be substituted by one or more non-aromatic radicals $R^3$, or a combination of these systems, where two radicals R may be linked to one another and may form an aliphatic or aromatic ring system.

In a particularly preferred embodiment of the invention, R is on each occurrence, identically or differently, H, D, C(=O)$R^3$, CN, Si($R^3$)$_3$, COO$R^3$, CON($R^3$)$_2$ or an aromatic or heteroaromatic ring system having 5 to 20 aromatic ring atoms, which may in each case be substituted by one or more non-aromatic radicals $R^3$, or an aryloxy or heteroaryloxy group having 5 to 20 aromatic ring atoms, which may be substituted by one or more non-aromatic radicals $R^3$.

R is very particularly preferably selected on each occurrence, identically or differently, from H, D or an aromatic or heteroaromatic ring system having 5 to 14 aromatic ring atoms, which may in each case be substituted by one or more non-aromatic radicals $R^3$.

In a further preferred embodiment of the invention, the radicals R are identical.

In a preferred embodiment of the invention, $R^1$ is on each occurrence, identically or differently, a straight-chain alkyl group having 1 to 20 C atoms or a branched or cyclic alkyl group having 3 to 20 C atoms or an alkenyl or alkynyl group having 2 to 20 C atoms, where one or more CH$_2$ groups in the above-mentioned alkyl, alkenyl and alkynyl groups may be replaced by Si($R^3$)$_2$, C=O, N$R^3$, —O—, —S—, —COO— or —CON$R^3$— and the above-mentioned alkyl, alkenyl and alkynyl groups may be substituted by one or more groups $R^3$ and where two or more radicals $R^1$ may be linked to one another and may form a ring system.

In a particularly preferred embodiment of the invention, $R^1$ is on each occurrence, identically or differently, a straight-chain alkyl group having 1 to 10 C atoms or a branched or cyclic alkyl group having 3 to 10 C atoms, where one or more $CH_2$ groups in the above-mentioned alkyl groups may be replaced by $Si(R^3)_2$, C=O, $NR^3$, —O—, —S—, —COO— or —$CONR^3$— and the above-mentioned alkyl groups may be substituted by one or more groups $R^3$.

In a very particularly preferred embodiment of the invention, $R^1$ is on each occurrence, identically or differently, a straight-chain alkyl group having 1 to 8 C atoms or a branched or cyclic alkyl group having 3 to 8 C atoms, where, of these, very particular preference is given to methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl and 2-ethylhexyl, in particular methyl.

In a further preferred embodiment of the invention, $R^2$ is on each occurrence, identically or differently, H, D, F, CN, $Si(R^3)_3$, $N(Ar_2)$, $N(R^3)_2$ or a straight-chain alkyl or alkoxy group having 1 to 20 C atoms or a branched or cyclic alkyl or alkoxy group having 3 to 20 C atoms, each of which may be substituted by one or more radicals $R^3$, where one or more adjacent or non-adjacent $CH_2$ groups may be replaced by —C≡C—, —$R^3$C=$CR^3$—, $Si(R^3)_2$, C=O, C=$NR^3$, —$NR^3$—, —O—, —S—, —COO— or —$CONR^3$—, or an aryl or heteroaryl group having 5 to 20 aromatic ring atoms, which may in each case be substituted by one or more radicals $R^3$, where two or more radicals $R^2$ may be linked to one another and may form an aliphatic or aromatic ring system.

$R^2$ is particularly preferably equal to H or D, $R^2$ is very particularly preferably equal to H.

In a further preferred embodiment of the invention, Ar is on each occurrence, identically or differently, an aryl or heteroaryl group having 5 to 30 aromatic C atoms, which may be substituted by one or more groups $R^3$.

The preferred embodiments described in the preceding sections can, in accordance with the invention, be combined with one another as desired. In particular, the preferred embodiments of the groups R, $R^1$ and $R^2$ can be combined with the preferred embodiments of the compounds of the formula (II) according to the invention. Furthermore, combination of the preferred embodiments of the groups X with the preferred embodiments of the groups R, $R^1$ and $R^2$ is a preferred embodiment of the invention.

Examples of compounds according to the invention are given in the following table.

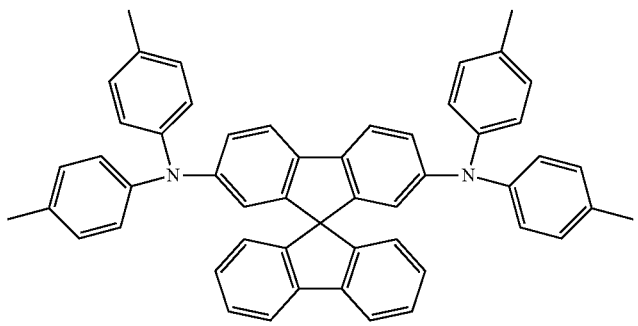

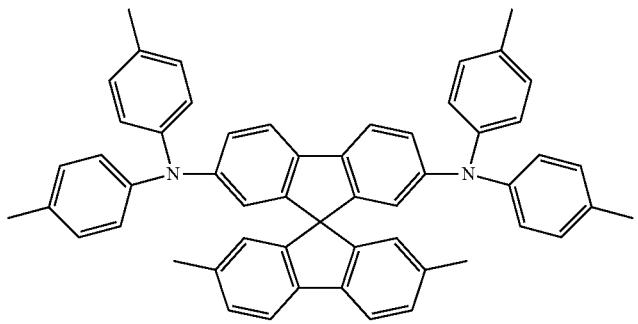

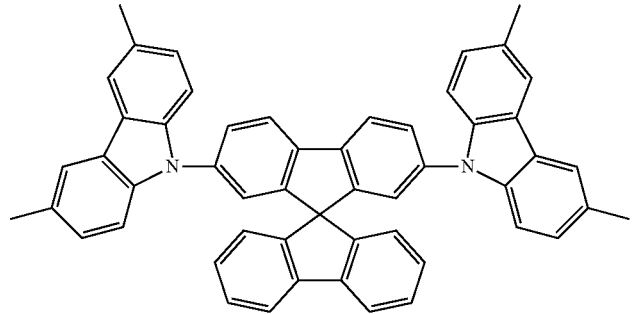

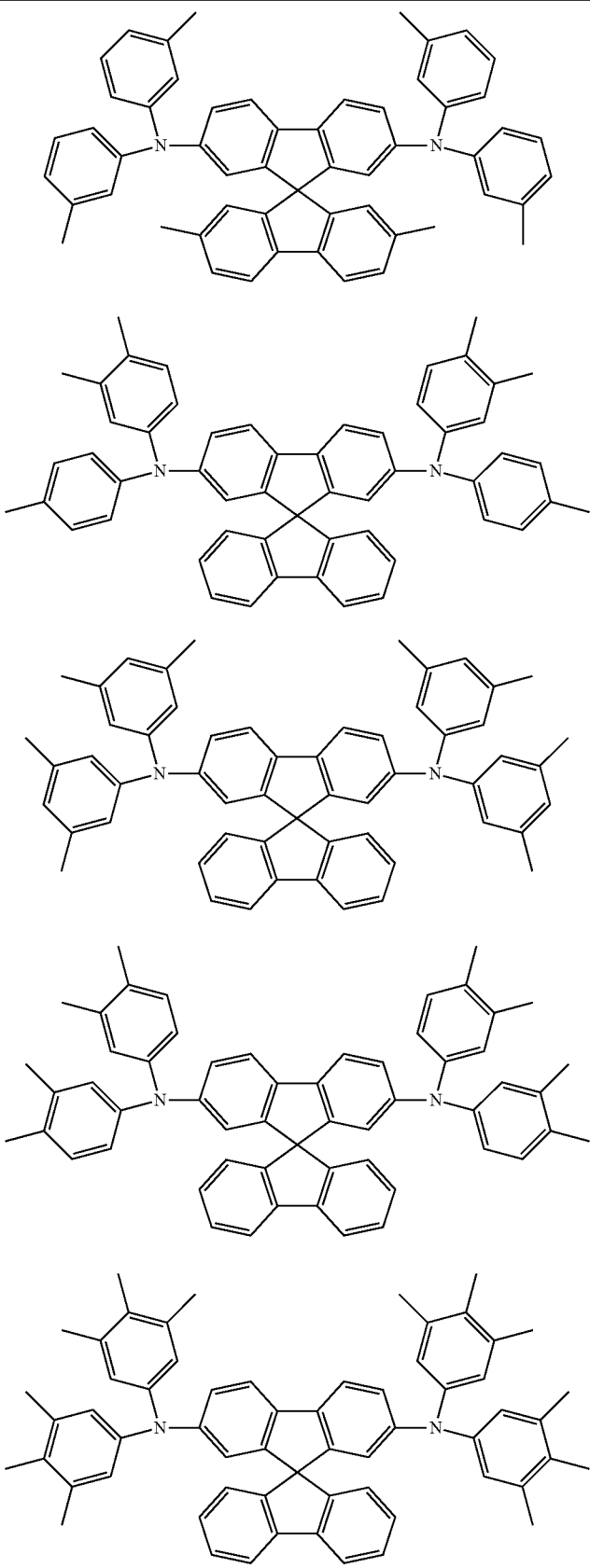

-continued
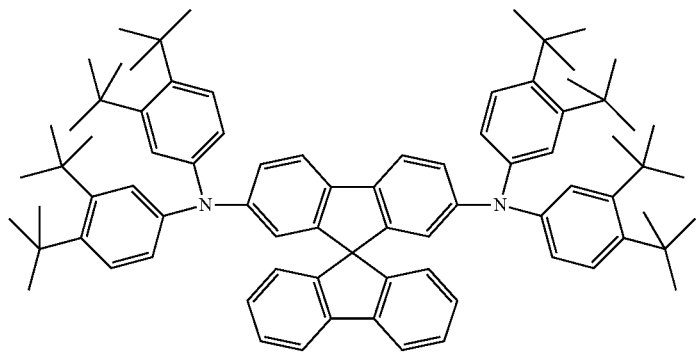 [SMILES: CC(C)(C)c1ccc(N(c2ccc(C(C)(C)C)c(C(C)(C)C)c2)c2ccc3c(c2)C2(c4ccccc4-c4ccccc42)c2cc(N(c4ccc(C(C)(C)C)c(C(C)(C)C)c4)c4ccc(C(C)(C)C)c(C(C)(C)C)c4)ccc2-3)cc1C(C)(C)C]
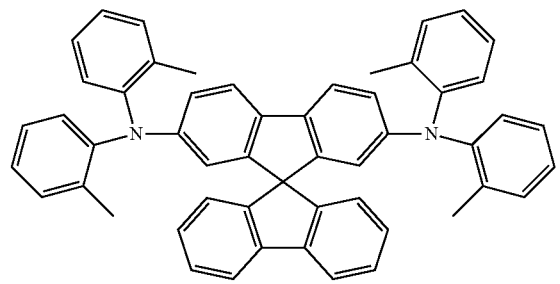 [SMILES: Cc1ccccc1N(c1ccc2c(c1)C1(c3ccccc3-c3ccccc31)c1cc(N(c3ccccc3C)c3ccccc3C)ccc1-2)c1ccccc1C]
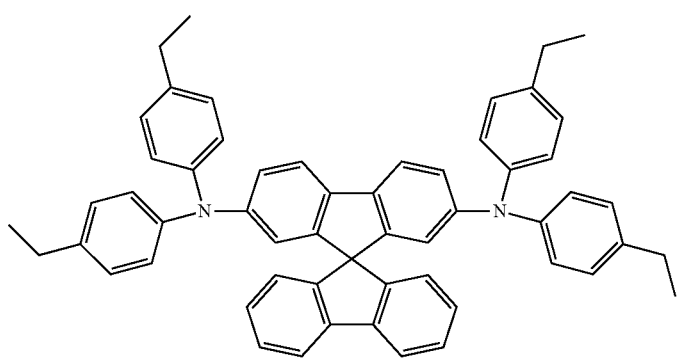 [SMILES: CCc1ccc(N(c2ccc(CC)cc2)c2ccc3c(c2)C2(c4ccccc4-c4ccccc42)c2cc(N(c4ccc(CC)cc4)c4ccc(CC)cc4)ccc2-3)cc1]
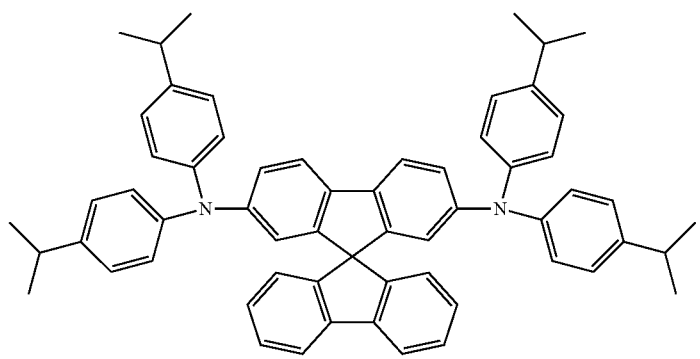 [SMILES: CC(C)c1ccc(N(c2ccc(C(C)C)cc2)c2ccc3c(c2)C2(c4ccccc4-c4ccccc42)c2cc(N(c4ccc(C(C)C)cc4)c4ccc(C(C)C)cc4)ccc2-3)cc1]

-continued
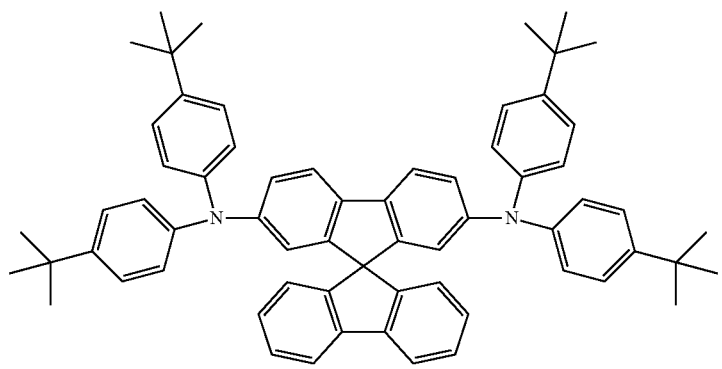 [SMILES: CC(C)(C)c1ccc(N(c2ccc(C(C)(C)C)cc2)c2ccc3c(c2)C2(c4ccccc4-c4ccccc42)c2cc(N(c4ccc(C(C)(C)C)cc4)c4ccc(C(C)(C)C)cc4)ccc2-3)cc1]
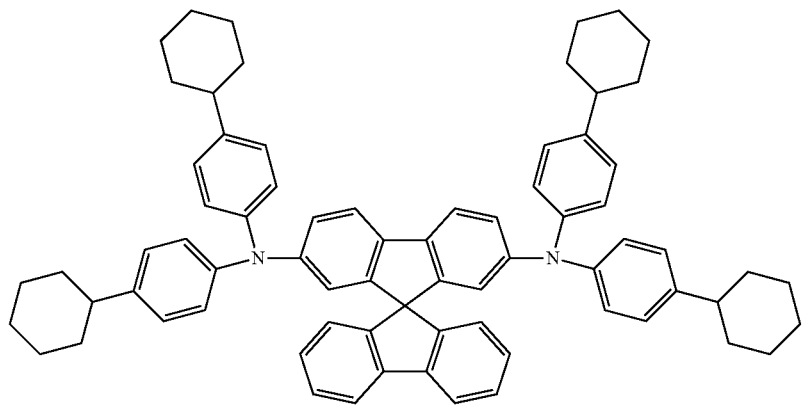 [SMILES: c1ccc2c(c1)-c1ccccc1C21c2cc(N(c3ccc(C4CCCCC4)cc3)c3ccc(C4CCCCC4)cc3)ccc2-c2ccc(N(c3ccc(C4CCCCC4)cc3)c3ccc(C4CCCCC4)cc3)cc21]
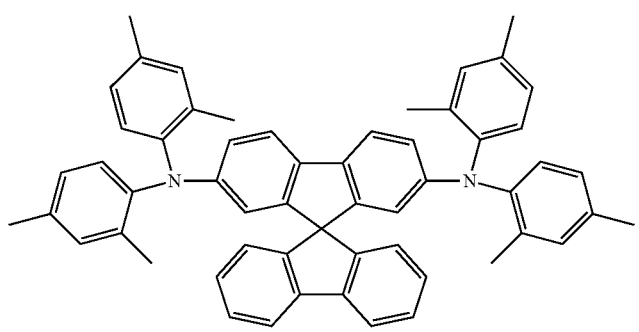
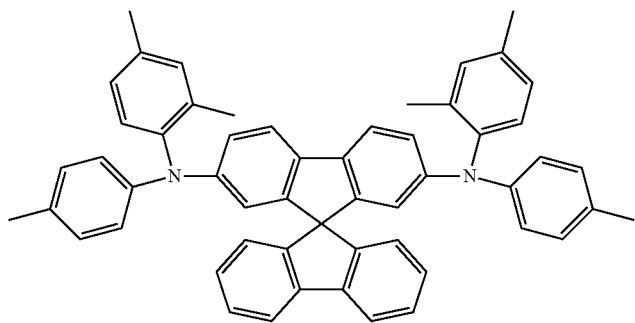

-continued
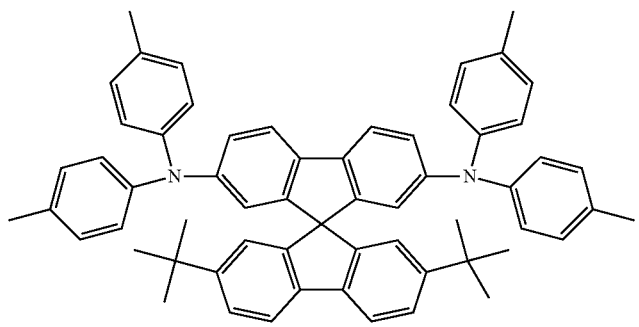
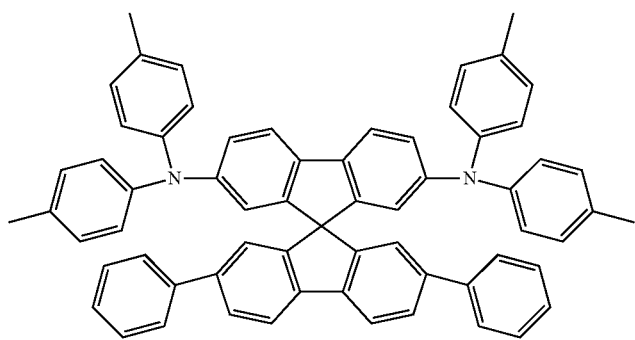
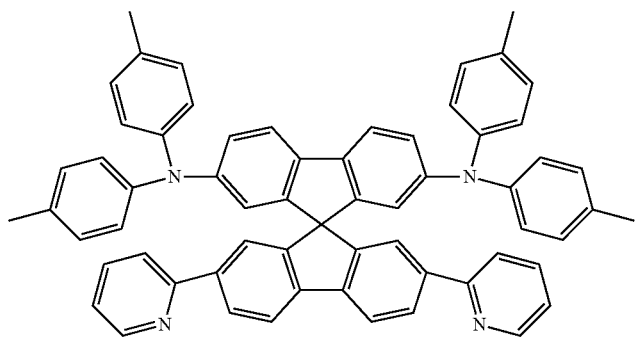
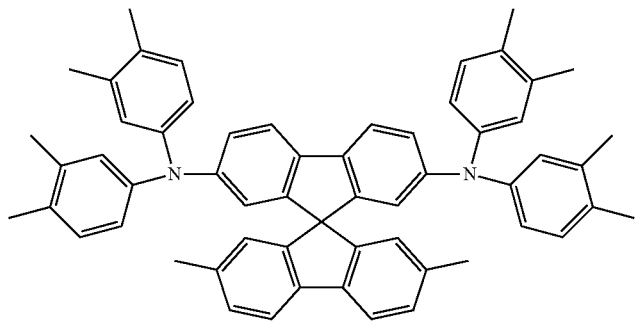

-continued
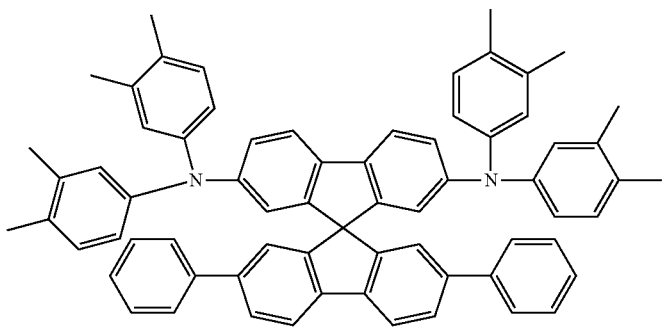
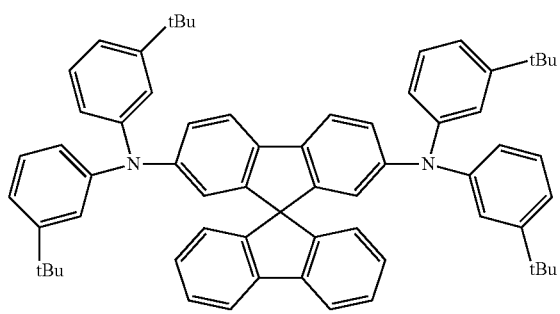 [SMILES: CC(C)(C)c1cccc(N(c2cccc(C(C)(C)C)c2)c2ccc3c(c2)C2(c4ccccc4-c4ccccc42)c2cc(N(c4cccc(C(C)(C)C)c4)c4cccc(C(C)(C)C)c4)ccc2-3)c1]
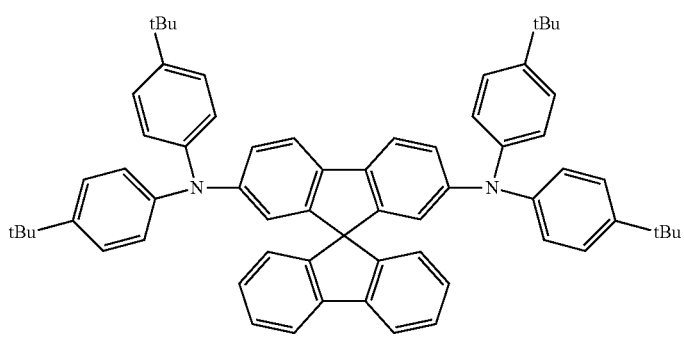 [SMILES: CC(C)(C)c1ccc(N(c2ccc(C(C)(C)C)cc2)c2ccc3c(c2)C2(c4ccccc4-c4ccccc42)c2cc(N(c4ccc(C(C)(C)C)cc4)c4ccc(C(C)(C)C)cc4)ccc2-3)cc1]
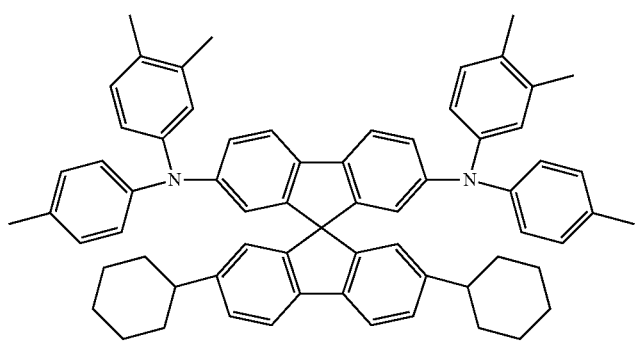
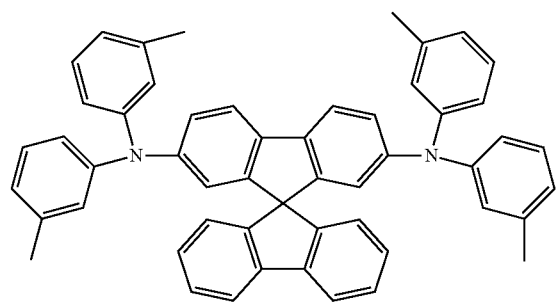 [SMILES: Cc1cccc(N(c2cccc(C)c2)c2ccc3c(c2)C2(c4ccccc4-c4ccccc42)c2cc(N(c4cccc(C)c4)c4cccc(C)c4)ccc2-3)c1]

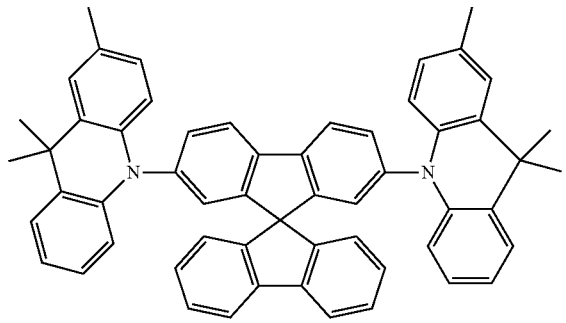

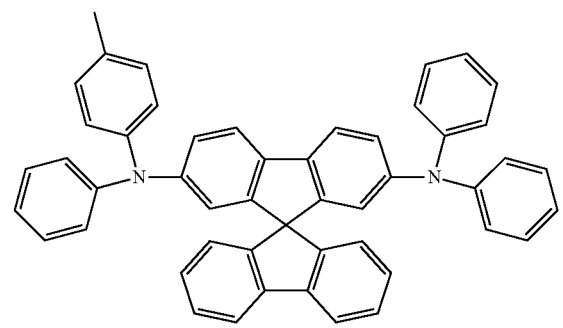 [SMILES: Cc1ccc(N(c2ccccc2)c2ccc3c(c2)C2(c4ccccc4-c4ccccc42)c2cc(N(c4ccccc4)c4ccccc4)ccc2-3)cc1]

The compounds according to the invention can be prepared by synthetic steps known to the person skilled in the art, such as, for example, bromination, Suzuki coupling, Hartwig-Buchwald coupling and further conventional reactions of organic synthesis.

The preparation of compounds according to the invention which are unsubstituted in the 2'- and 7'-positions can start, for example, from 2,7-dibromospirobifluorene (Beijing Aglaia Techn. Develop. Co.), which is reacted with a diphenylamine compound in a Hartwig-Buchwald coupling (Scheme 1, $R^1$ is as defined above and p can adopt, identically or differently, a value of 0 to 5, where all p cannot simultaneously be equal to zero). A multiplicity of differently substituted diphenylamines are either commercially available or their synthesis is known in the specialist literature.

For the preparation of compounds according to the invention which are substituted by an aryl or heteroaryl group in the 2'- and 7'-positions, the process depicted in Scheme 2, for example, can be followed. Ar in Scheme 2 stands for an aryl or heteroaryl group.

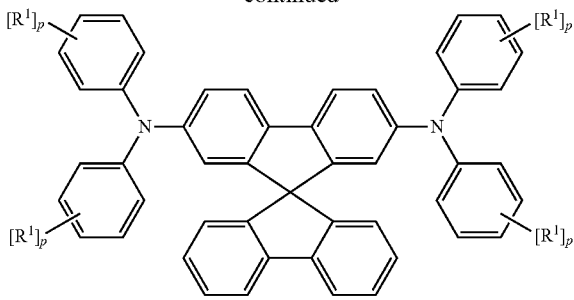

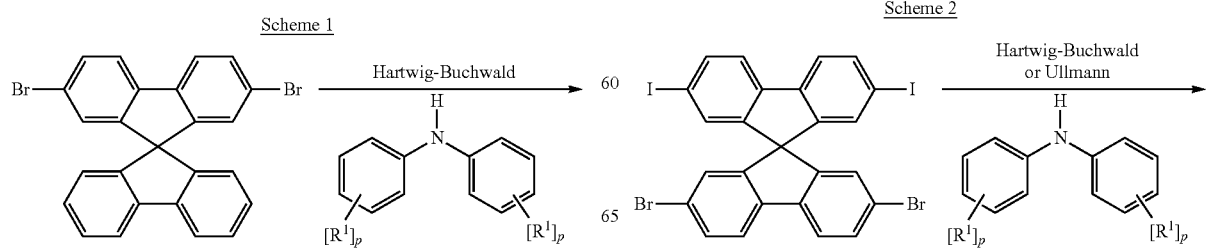

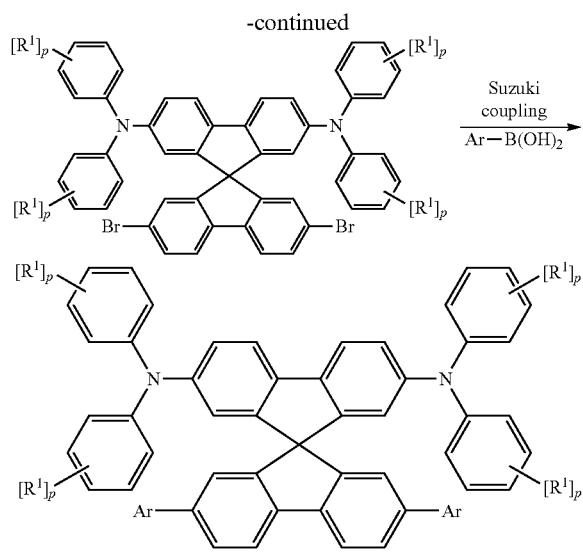

This process starts from 2,7-diiodo-2',7'-dibromospirobifluorene, the synthesis of which is described in the application WO 2003/020790. Firstly, the spirobifluorene is reacted with a diarylamino compound (cf. above) in a Hartwig-Buchwald coupling or an Ullmann reaction. In a second step, the groups Ar are subsequently introduced into positions 2' and 7' in a Suzuki coupling.

The invention thus relates to a process for the preparation of a compound of the formula (I) according to the invention, characterised in that at least one organometallic coupling reaction, preferably a Hartwig-Buchwald reaction, is employed for the introduction of one or more arylamino groups into a spirobifluorene derivative.

The invention also relates to formulations comprising at least one compound of the formula (I) and at least one solvent, preferably an organic solvent.

The formulations according to the invention are used, for example, in the production of organic electroluminescent devices.

The compounds of the formula (I) according to the invention are suitable for use in electronic devices, in particular in organic electroluminescent devices (OLEDs). Depending on the substitution, the compounds are employed in different functions and in different layers of the organic electroluminescent device. The compounds are preferably employed in a hole-transport and/or hole-injection layer. However, they can also be employed in other layers and/or functions, for example as fluorescent dopants in an emitting layer or as matrix materials for phosphorescent dopants in an emitting layer or in a outcoupling layer of the organic electroluminescent device.

The invention therefore furthermore relates to the use of the compounds of the formula (I) according to the invention in electronic devices. The electronic devices here are preferably selected from the group consisting of organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and particularly preferably organic electroluminescent devices (OLEDs).

The invention thus also relates to electronic devices, preferably organic electroluminescent devices, comprising one or more compounds of the formula (I).

Particular preference is given to organic electroluminescent devices comprising an anode, a cathode and at least one emitting layer, characterised in that at least one organic layer, which may be a hole-transport layer, an emitting layer or another layer, comprises at least one compound of the formula (I).

This layer does not necessarily have to be arranged between the electrodes.

Apart from the cathode, the anode and the emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, interlayers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*), organic or inorganic p/n junctions and/or outcoupling layers. However, it should be pointed out that each of these layers does not necessarily have to be present, and the choice of the layers is always dependent on the compounds used and in particular also on whether the device is a fluorescent or phosphorescent electroluminescent device.

In a further embodiment of the invention, the organic electroluminescent device comprises a plurality of emitting layers. The emitting layers in this case particularly preferably have in total a plurality of emission maxima between 380 nm and 750 nm, resulting overall in white emission, i.e. various emitting compounds which are able to fluoresce or phosphoresce and which emit blue and yellow, orange or red light are used in the emitting layers. Particular preference is given to three-layer systems, i.e. systems having three emitting layers, where at least one of these layers comprises at least one compound of the formula (I) and where the three layers exhibit blue, green and orange or red emission (for the basic structure see, for example, WO 05/011013). Emitters which have broad-band emission bands and thus exhibit white emission are likewise suitable for white emission. The compounds according to the invention may in such devices also be present in the hole-transport layer and/or in a different layer.

In a preferred embodiment of the invention, the compound of the formula (I) is employed in an electronic device comprising one or more phosphorescent dopants. The compound here can be used in various layers, preferably in a hole-transport layer, a hole-injection layer or in an emitting layer. However, the compound of the formula (I) can also be employed in accordance with the invention in an electronic device comprising one or more fluorescent dopants.

Suitable phosphorescent dopants (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as being phosphorescent compounds.

Examples of the emitters described above are disclosed in the applications WO 00/70655, WO 01/41512, WO 02/02714, WO 02/15645, EP 1191613, EP 1191612, EP 1191614, WO 05/033244, WO 05/019373 and US 2005/

0258742. In general, all phosphorescent complexes as used in accordance with the prior art for phosphorescent OLEDs and as are known to the person skilled in the art in the area of organic electroluminescent devices are suitable. The person skilled in the art will also be able to employ further phosphorescent complexes, without inventive step, in combination with the compounds of the formula (I) according to the invention in organic electroluminescent devices.

In a preferred embodiment of the invention, the compounds of the formula (I) are employed as hole-transport material or hole-injection material. The compounds are then preferably employed in a hole-transport layer and/or in a hole-injection layer. For the purposes of this invention, a hole-injection layer is a layer which is directly adjacent to the anode. For the purposes of this invention, a hole-transport layer is a layer which is located between the hole-injection layer and the emission layer. The hole-transport layer may be directly adjacent to the emission layer. If the compounds of the formula (I) are used as hole-transport material or as hole-injection material, it may be preferred for them to be doped with electron-acceptor compounds, for example with $F_4$-TCNQ or with compounds as described in EP 1476881 or EP 1596445. In a further preferred embodiment of the invention, a compound of the formula (I) is used as hole-transport material in combination with a hexaazatriphenylene derivative, as described in US 2007/0092755. The hexaazatriphenylene derivative is particularly preferably employed in a separate layer here.

Thus, for example, preference is given to a structure which has the following construction: anode—hexaazatriphenylene derivative—hole-transport layer, where the hole-transport layer comprises one or more compounds of the formula (I). It is likewise possible in this construction to use a plurality of successive hole-transport layers, where at least one hole-transport layer comprises at least one compound of the formula (I). The following structure construction is likewise preferred: anode—hole-transport layer—hexaazatriphenylene derivative—hole-transport layer, where at least one of the two hole-transport layers comprises one or more compounds of the formula (I). It is likewise possible in this construction to use a plurality of successive hole-transport layers instead of one hole-transport layer, where at least one hole-transport layer comprises at least one compound of the formula (I).

If the compound of the formula (I) is employed as hole-transport material in a hole-transport layer, the compound can be employed as pure material, i.e. in a proportion of 100% in the hole-transport layer, or it can be employed in combination with one or more further compounds in the hole-transport layer, as described, for example, in the unpublished application DE 102010010481.7.

The invention thus furthermore relates to mixtures comprising one or more compounds of the formula (I) and one or more further compounds, which are preferably selected from electron-acceptor compounds, such as, for example, $F_4$-TCNQ. The mixtures are preferably used in the hole-transport layer and/or hole-injection layer of organic electroluminescent devices.

In a further embodiment of the present invention, the compounds of the formula (I) are employed as matrix material in combination with one or more dopants, preferably phosphorescent dopants.

A dopant is taken to mean the component whose proportion in the mixture is the smaller in a system comprising a matrix material and a dopant. Correspondingly, a matrix material is taken to mean the component whose proportion in the mixture is the greater in a system comprising a matrix material and a dopant.

The proportion of the matrix material in the emitting layer is in this case between 50.0 and 99.9% by vol., preferably between 80.0 and 99.5% by vol. and particularly preferably between 92.0 and 99.5% by vol. for fluorescent emitting layers and between 85.0 and 97.0% by vol. for phosphorescent emitting layers.

Correspondingly, the proportion of the dopant is between 0.1 and 50.0% by vol., preferably between 0.5 and 20.0% by vol. and particularly preferably between 0.5 and 8.0% by vol. for fluorescent emitting layers and between 3.0 and 15.0% by vol. for phosphorescent emitting layers.

An emitting layer of an organic electroluminescent device may also comprise systems comprising a plurality of matrix materials (mixed matrix systems) and/or a plurality of dopants. In this case too, the dopants are generally the materials whose proportion in the system is the smaller and the matrix materials are the materials whose proportion in the system is the greater. In individual cases, however, the proportion of an individual matrix material in the system may be smaller than the proportion of an individual dopant.

In a preferred embodiment of the invention, the compounds of the formula (I) are used as a component of mixed matrix systems. The mixed matrix systems preferably comprise two or three different matrix materials, particularly preferably two different matrix materials. The two different matrix materials here may be present in a ratio of 1:10 to 1:1, preferably in a ratio of 1:4 to 1:1. The mixed matrix systems may comprise one or more dopants. The dopant compound or the dopant compounds together have, in accordance with the invention, a proportion of 0.1 to 50.0% by vol. in the mixture as a whole and preferably a proportion of 0.5 to 20.0% by vol. in the mixture as a whole. Correspondingly, the matrix components together have a proportion of 50.0 to 99.9% by vol. in the mixture as a whole and preferably a proportion of 80.0 to 99.5% by vol. in the mixture as a whole.

Mixed matrix systems are preferably employed in phosphorescent organic electroluminescent devices.

Particularly suitable matrix materials, which can be employed in combination with the compounds according to the invention as matrix components of a mixed matrix system, are aromatic ketones, aromatic phosphine oxides or aromatic sulfoxides or sulfones, for example in accordance with WO 04/013080, WO 04/093207, WO 06/005627 or DE 102008033943, triarylamines, carbazole derivatives, for example CBP (N,N-biscarbazolylbiphenyl) or the carbazole derivatives disclosed in WO 05/039246, US 2005/0069729, JP 2004/288381, EP 1205527 or WO 08/086851, indolocarbazole derivatives, for example in accordance with WO 07/063754 or WO 08/056746, azacarbazole derivatives, for example in accordance with EP 1617710, EP 1617711, EP 1731584, JP 2005/347160, bipolar matrix materials, for example in accordance with WO 07/137725, silanes, for example in accordance with WO 05/111172, azaboroles or boronic esters, for example in accordance with WO 06/117052, triazine derivatives, for example in accordance with DE 102008036982, WO 07/063754 or WO 08/056746, zinc complexes, for example in accordance with EP 652273 or WO 09/062578, diazasilole or tetraazasilole derivatives, for example in accordance with WO 2010/054729, diazaphosphole derivatives, for example in accordance with WO 2010/054730, or indenocarbazole derivatives, for example in accordance with WO 2010/136109.

Preferred phosphorescent dopants for use in mixed matrix systems comprising the compounds according to the invention are the phosphorescent dopants mentioned above.

The invention thus furthermore relates to mixtures comprising one or more compounds of the formula (I) and one or more further compounds selected from phosphorescent dopants and/or further matrix materials, preferably aromatic ketones, aromatic phosphine oxides or aromatic sulfoxides or sulfones, triarylamines, carbazole derivatives, indolocarbazole derivatives, azacarbazole derivatives, bipolar matrix materials, silanes, azaboroles or boronic esters, triazine derivatives, zinc complexes, diazasilole or tetraazasilole derivatives, diazaphosphole derivatives and indenocarbazole derivatives.

In a further embodiment of the invention, the compounds of the formula (I) are employed as fluorescent emitting materials in an emitting layer. In this case, the compounds according to the invention are particularly preferably used as green or blue emitters.

Preferred matrix materials for use in combination with the compounds according to the invention as fluorescent emitters are mentioned in one of the following sections. They correspond to the matrix materials mentioned as preferred below for fluorescent emitters.

In a further preferred embodiment of the invention, the compounds of the formula (I) are used as optical outcoupling material in a outcoupling layer.

The outcoupling layer is applied to the side of one of the two electrodes which faces away from the electroluminescent layer and improves the outcoupling of the light emitted by the device. The electrode to which the outcoupling layer is applied is transparent or partially transparent and may either be the anode or the cathode of the organic electroluminescent device.

The outcoupling layer preferably has a thickness in the range 10-200 nm, particularly preferably in the range 30-100 nm. Materials according to the invention which have a high glass transition temperature are preferably used in the outcoupling layer. The glass transition temperature of the materials used in the outcoupling layer is preferably above 120° C., particularly preferably above 150° C. The materials according to the invention used in the outcoupling layer furthermore preferably have low, preferably negligible, absorption in the visible wavelength region. The absorbance of the compounds in the range 400-700 nm is preferably less than 0.05, particularly preferably less than 0.01 and very particularly preferably less than 0.001.

The materials preferably employed in the electronic devices according to the invention for the respective functions or in the respective functional layers are mentioned below.

Preferred fluorescent emitter materials are selected from the class of the monostyrylamines, the distyrylamines, the tristyrylamines, the tetrastyrylamines, the styrylphosphines, the styryl ethers and the arylamines. A monostyrylamine is taken to mean a compound which contains one substituted or unsubstituted styryl group and at least one, preferably aromatic, amine. A distyrylamine is taken to mean a compound which contains two substituted or unsubstituted styryl groups and at least one, preferably aromatic, amine. A tristyrylamine is taken to mean a compound which contains three substituted or unsubstituted styryl groups and at least one, preferably aromatic, amine. A tetrastyrylamine is taken to mean a compound which contains four substituted or unsubstituted styryl groups and at least one, preferably aromatic, amine. The styryl groups are particularly preferably stilbenes, which may also be further substituted. Corresponding phosphines and ethers are defined analogously to the amines. For the purposes of this invention, an arylamine or an aromatic amine is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred emitter materials are selected from indenofluorenamines or indenofluorenediamines, for example in accordance with WO 06/122630, benzoindenofluorenamines or benzoindenofluorenediamines, for example in accordance with WO 08/006449, and dibenzoindenofluorenamines or dibenzoindenofluorenediamines, for example in accordance with WO 07/140847. Examples of emitter materials from the class of the styrylamines are substituted or unsubstituted tristilbenamines or the emitter materials described in WO 06/000388, WO 06/058737, WO 06/000389, WO 07/065549 and WO 07/115610. Preference is furthermore given to the condensed hydrocarbons disclosed in the application DE 102008035413.

Preferred fluorescent emitter materials are furthermore the compounds of the formula (I) according to the invention.

Suitable emitter materials are furthermore the structures depicted in the following table, and the derivatives of these structures disclosed in JP 06/001973, WO 04/047499, WO 06/098080, WO 07/065678, US 2005/0260442 and WO 04/092111.

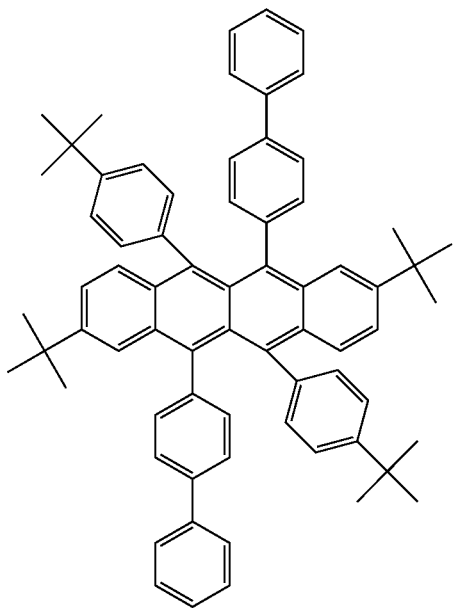 [SMILES: CC(C)(C)c1ccc(-c2c3ccc(C(C)(C)C)cc3c(-c3ccc(-c4ccccc4)cc3)c3c(-c4ccc(C(C)(C)C)cc4)c4ccc(C(C)(C)C)cc4c(-c4ccc(-c5ccccc5)cc4)c23)cc1]
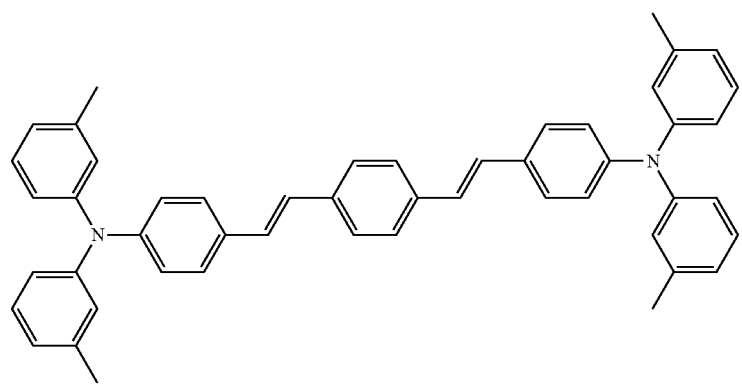 [SMILES: Cc1cccc(N(c2ccc(/C=C/c3ccc(/C=C/c4ccc(N(c5cccc(C)c5)c5cccc(C)c5)cc4)cc3)cc2)c2cccc(C)c2)c1]
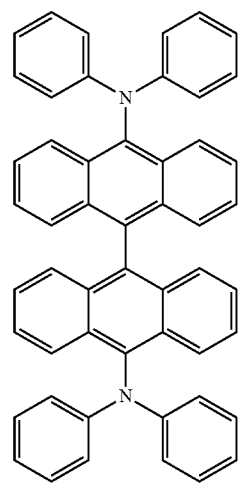 [SMILES: c1ccc(N(c2ccccc2)c2c3ccccc3c(-c3c4ccccc4c(N(c4ccccc4)c4ccccc4)c4ccccc34)c3ccccc23)cc1]

-continued
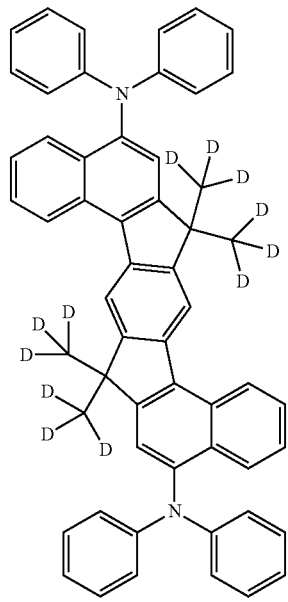 [SMILES: [2H]C([2H])([2H])C1(C([2H])([2H])[2H])c2cc3c(cc2-c2c1cc(N(c1ccccc1)c1ccccc1)c1ccccc21)C(C([2H])([2H])[2H])(C([2H])([2H])[2H])c1cc(N(c2ccccc2)c2ccccc2)c2ccccc2c1-3]
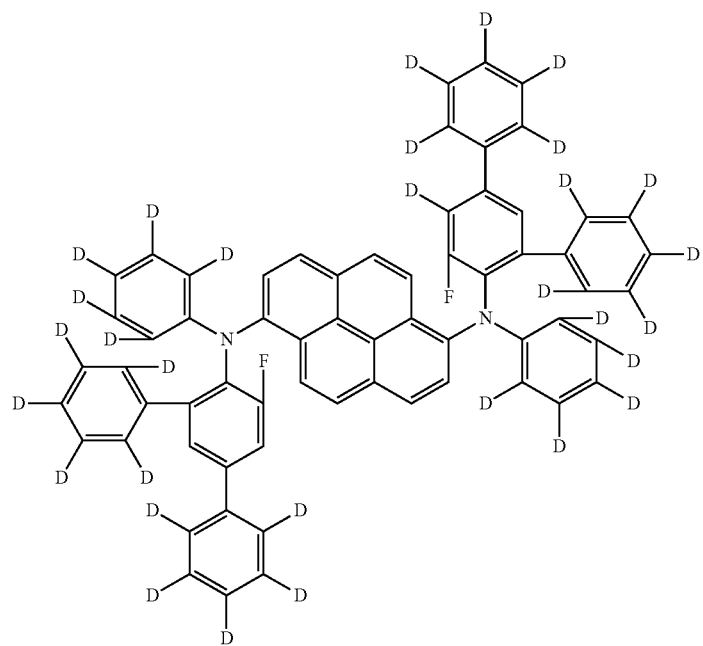 [SMILES: [2H]c1c([2H])c([2H])c(-c2cc(F)c(N(c3c([2H])c([2H])c([2H])c([2H])c3[2H])c3ccc4ccc5c(N(c6c([2H])c([2H])c([2H])c([2H])c6[2H])c6c(-c7c([2H])c([2H])c([2H])c([2H])c7[2H])cc(-c7c([2H])c([2H])c([2H])c([2H])c7[2H])c([2H])c6F)ccc6ccc3c4c65)c(-c3c([2H])c([2H])c([2H])c([2H])c3[2H])c2)c([2H])c1[2H]]
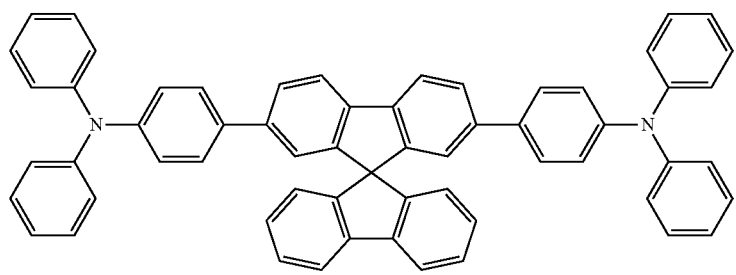 [SMILES: c1ccc(N(c2ccccc2)c2ccc(-c3ccc4c(c3)C3(c5ccccc5-c5ccccc53)c3cc(-c5ccc(N(c6ccccc6)c6ccccc6)cc5)ccc3-4)cc2)cc1]

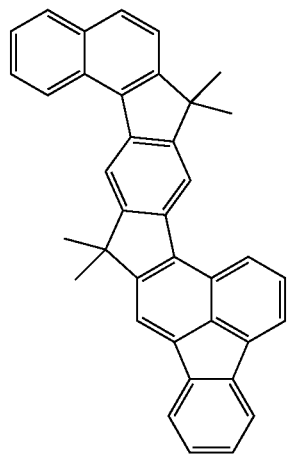 [SMILES: CC1(C)c2cc3c(cc2-c2c1ccc1ccccc21)C(C)(C)c1cc2c4c(cccc4c1-3)-c1ccccc1-2]
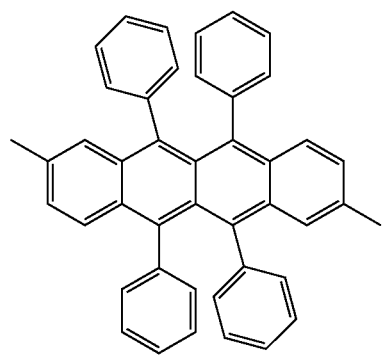
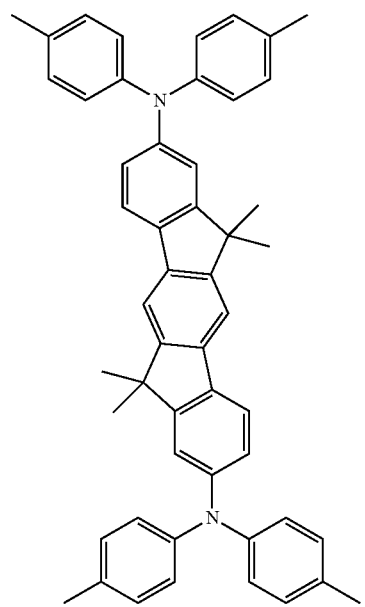

-continued
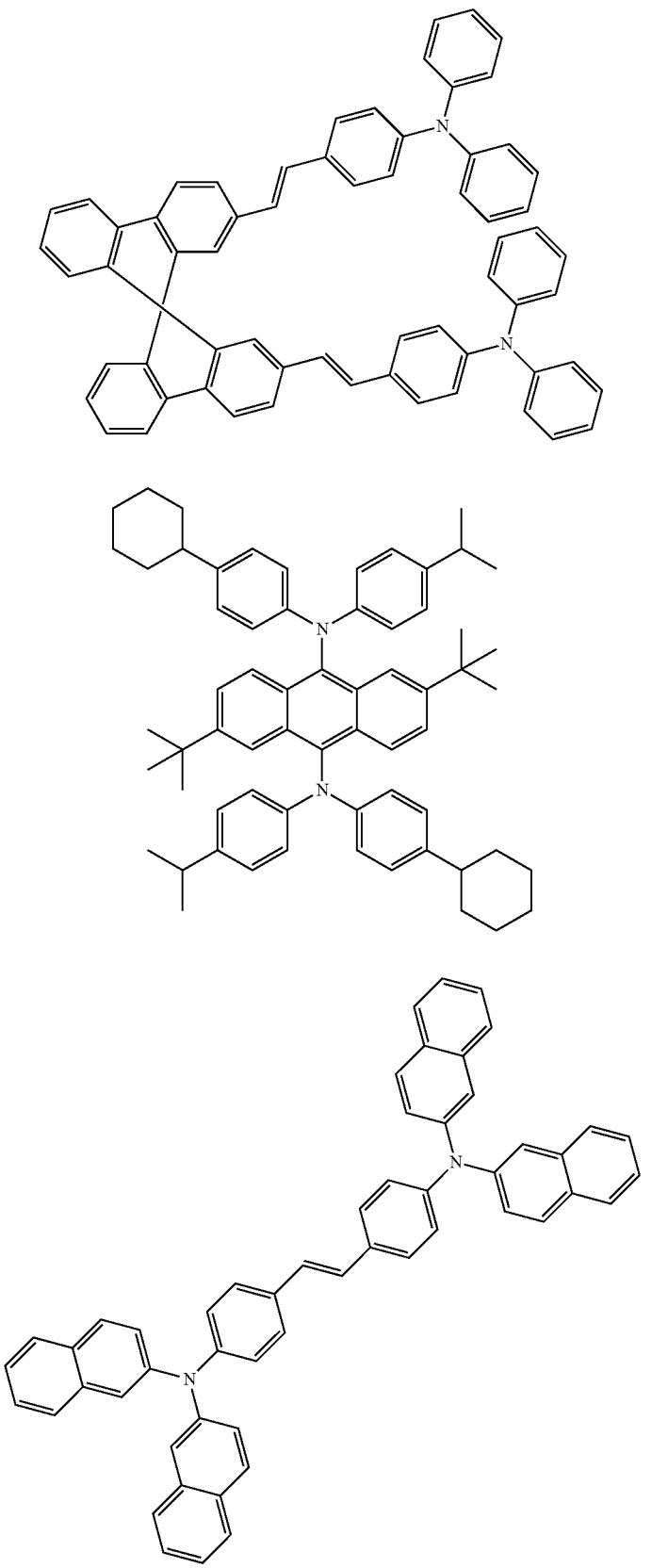

-continued
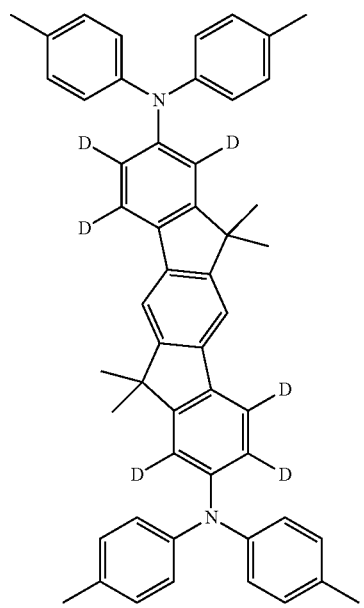
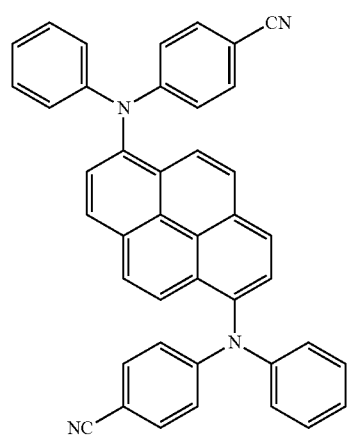 [SMILES: N#Cc1ccc(N(c2ccccc2)c2ccc3ccc4c(N(c5ccccc5)c5ccc(C#N)cc5)ccc5ccc2c3c54)cc1]

-continued
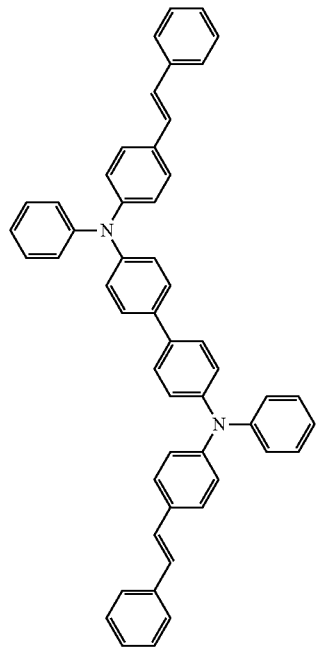 [SMILES: C(=C\c1ccc(N(c2ccccc2)c2ccc(-c3ccc(N(c4ccccc4)c4ccc(/C=C/c5ccccc5)cc4)cc3)cc2)cc1)/c1ccccc1]
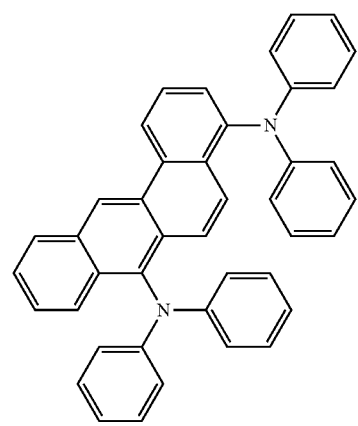 [SMILES: c1ccc(N(c2ccccc2)c2cccc3c2ccc2c(N(c4ccccc4)c4ccccc4)c4ccccc4cc23)cc1]
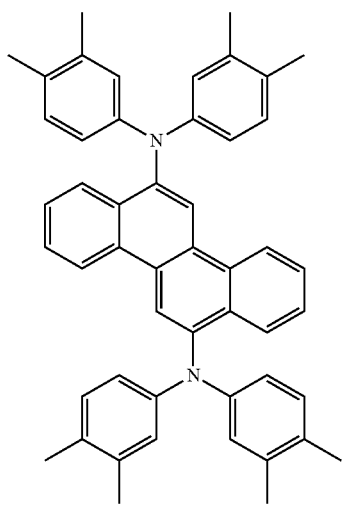

-continued
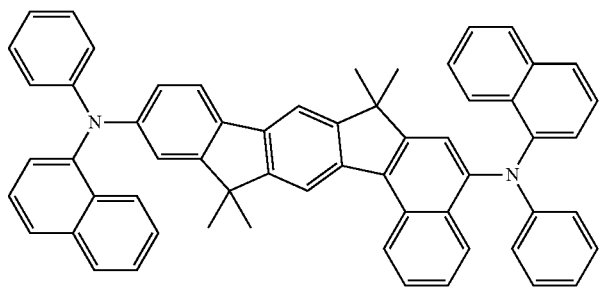 [SMILES: CC1(C)c2cc(N(c3ccccc3)c3cccc4ccccc34)ccc2-c2cc3c(cc21)-c1c(cc(N(c2ccccc2)c2cccc4ccccc24)c2ccccc12)C3(C)C]
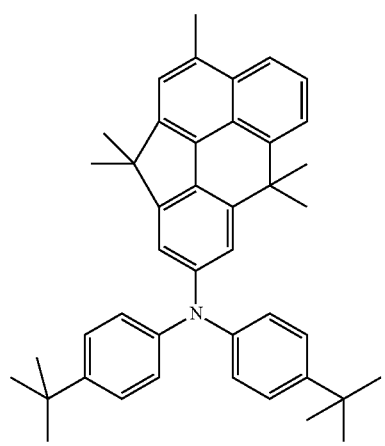 [SMILES: Cc1cc2c3c4c(cccc14)C(C)(C)c1cc(N(c4ccc(C(C)(C)C)cc4)c4ccc(C(C)(C)C)cc4)cc(c1-3)C2(C)C]
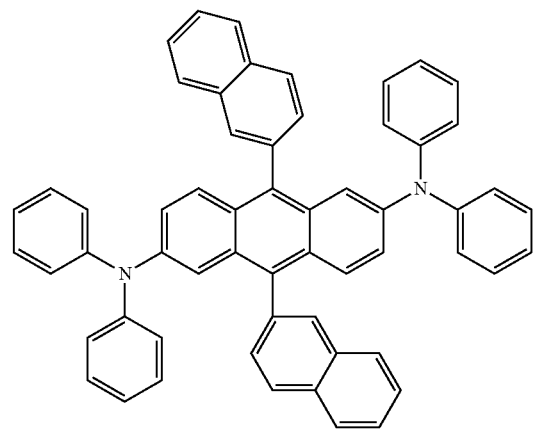 [SMILES: c1ccc(N(c2ccccc2)c2ccc3c(-c4ccc5ccccc5c4)c4cc(N(c5ccccc5)c5ccccc5)ccc4c(-c4ccc5ccccc5c4)c3c2)cc1]
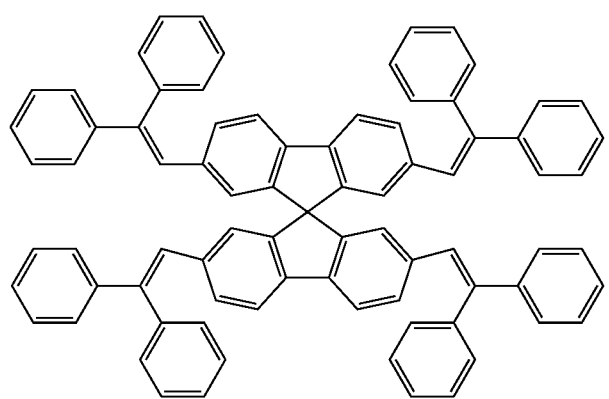 [SMILES: C(=C(c1ccccc1)c1ccccc1)c1ccc2c(c1)C1(c3cc(C=C(c4ccccc4)c4ccccc4)ccc3-2)c2cc(C=C(c3ccccc3)c3ccccc3)ccc2-c2ccc(C=C(c3ccccc3)c3ccccc3)cc21]

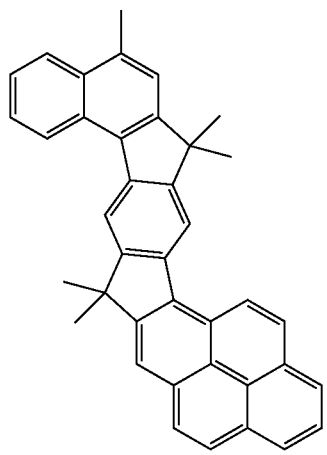 [SMILES: Cc1cc2c(c3ccccc13)-c1cc3c(cc1C2(C)C)-c1c(cc2ccc4cccc5ccc1c2c45)C3(C)C]
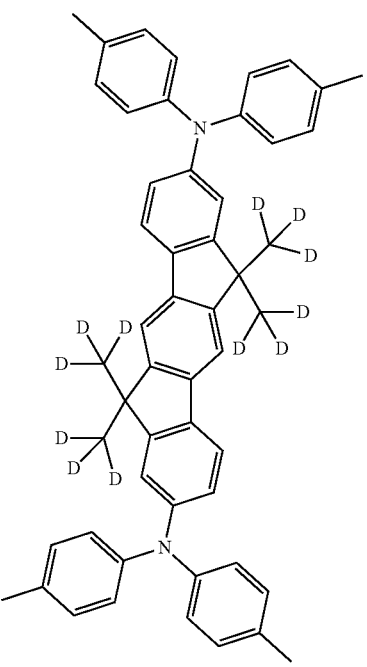
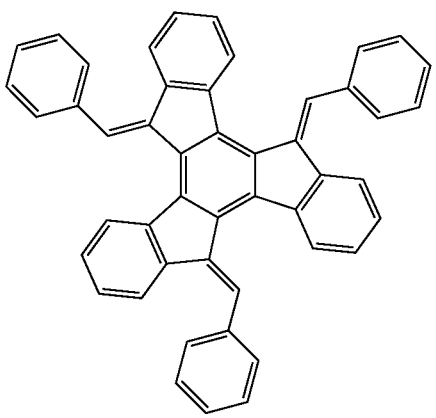 [SMILES: C(=C1/c2ccccc2-c2c1c1c(c3c2/C(=C/c2ccccc2)c2ccccc2-3)/C(=C/c2ccccc2)c2ccccc2-1)/c1ccccc1]

-continued
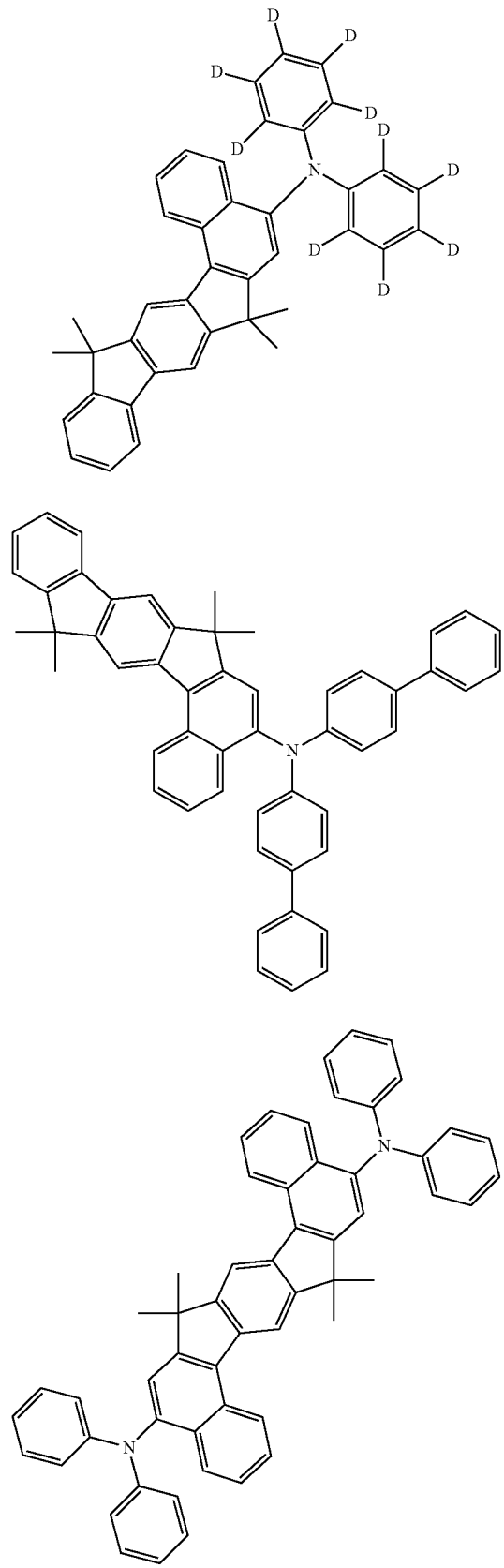

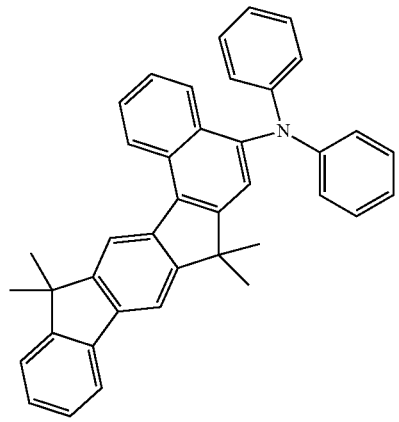 [SMILES: CC1(C)c2ccccc2-c2cc3c(cc21)-c1c(cc(N(c2ccccc2)c2ccccc2)c2ccccc12)C3(C)C]
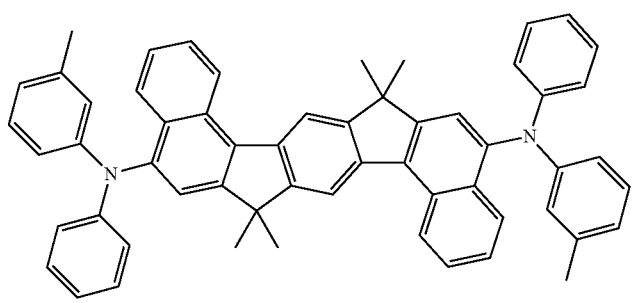 [SMILES: Cc1cccc(N(c2ccccc2)c2cc3c(c4ccccc24)-c2cc4c(cc2C3(C)C)-c2c(cc(N(c3ccccc3)c3cccc(C)c3)c3ccccc23)C4(C)C)c1]
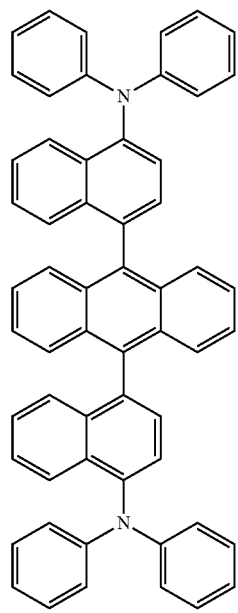 [SMILES: c1ccc(N(c2ccccc2)c2ccc(-c3c4ccccc4c(-c4ccc(N(c5ccccc5)c5ccccc5)c5ccccc45)c4ccccc34)c3ccccc23)cc1]

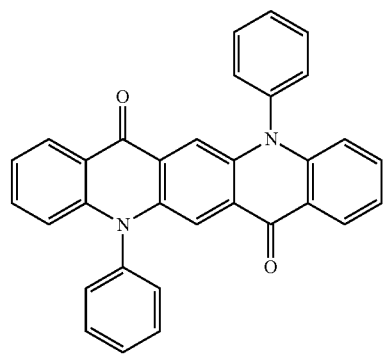 [SMILES: O=c1c2ccccc2n(-c2ccccc2)c2cc3c(=O)c4ccccc4n(-c4ccccc4)c3cc12]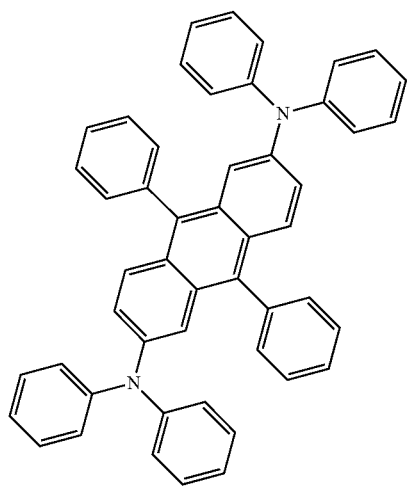 [SMILES: c1ccc(-c2c3ccc(N(c4ccccc4)c4ccccc4)cc3c(-c3ccccc3)c3ccc(N(c4ccccc4)c4ccccc4)cc23)cc1]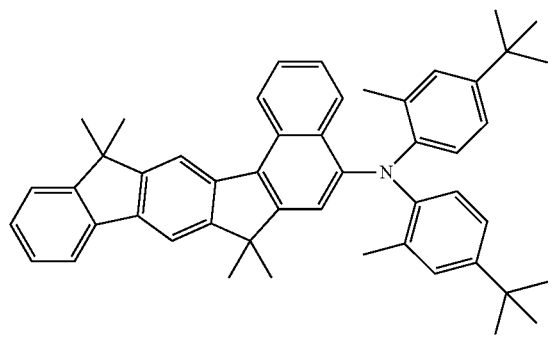 [SMILES: Cc1cc(C(C)(C)C)ccc1N(c1ccc(C(C)(C)C)cc1C)c1cc2c(c3ccccc13)-c1cc3c(cc1C2(C)C)-c1ccccc1C3(C)C]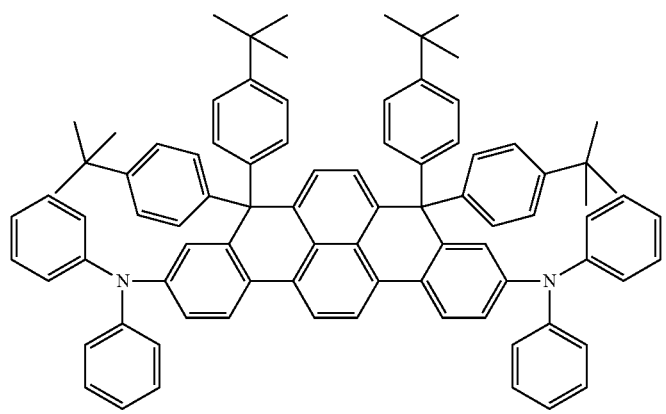 [SMILES: CC(C)(C)c1ccc(C2(c3ccc(C(C)(C)C)cc3)c3cc(N(c4ccccc4)c4ccccc4)ccc3-c3ccc4c5c(ccc2c35)C(c2ccc(C(C)(C)C)cc2)(c2ccc(C(C)(C)C)cc2)c2cc(N(c3ccccc3)c3ccccc3)ccc2-4)cc1]

-continued
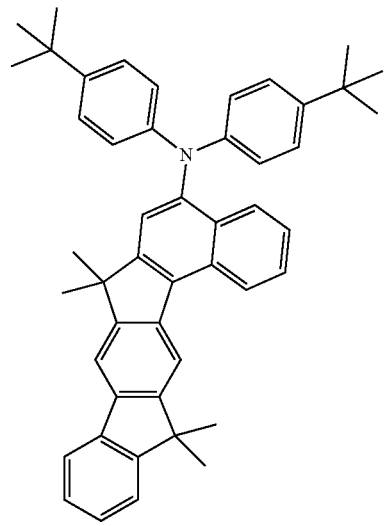 [SMILES: CC(C)(C)c1ccc(N(c2ccc(C(C)(C)C)cc2)c2cc3c(c4ccccc24)-c2cc4c(cc2C3(C)C)-c2ccccc2C4(C)C)cc1]
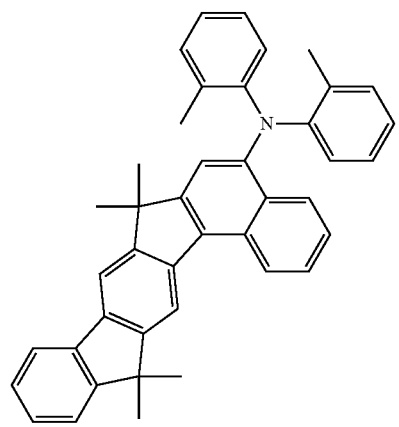 [SMILES: Cc1ccccc1N(c1ccccc1C)c1cc2c(c3ccccc13)-c1cc3c(cc1C2(C)C)-c1ccccc1C3(C)C]
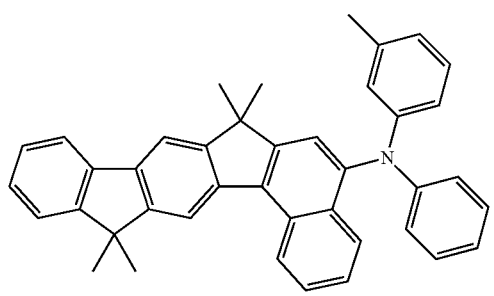 [SMILES: Cc1cccc(N(c2ccccc2)c2cc3c(c4ccccc24)-c2cc4c(cc2C3(C)C)-c2ccccc2C4(C)C)c1]
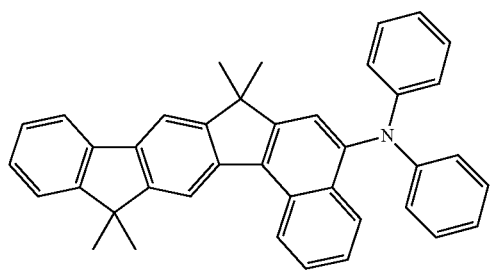 [SMILES: CC1(C)c2ccccc2-c2cc3c(cc21)-c1c(cc(N(c2ccccc2)c2ccccc2)c2ccccc12)C3(C)C]

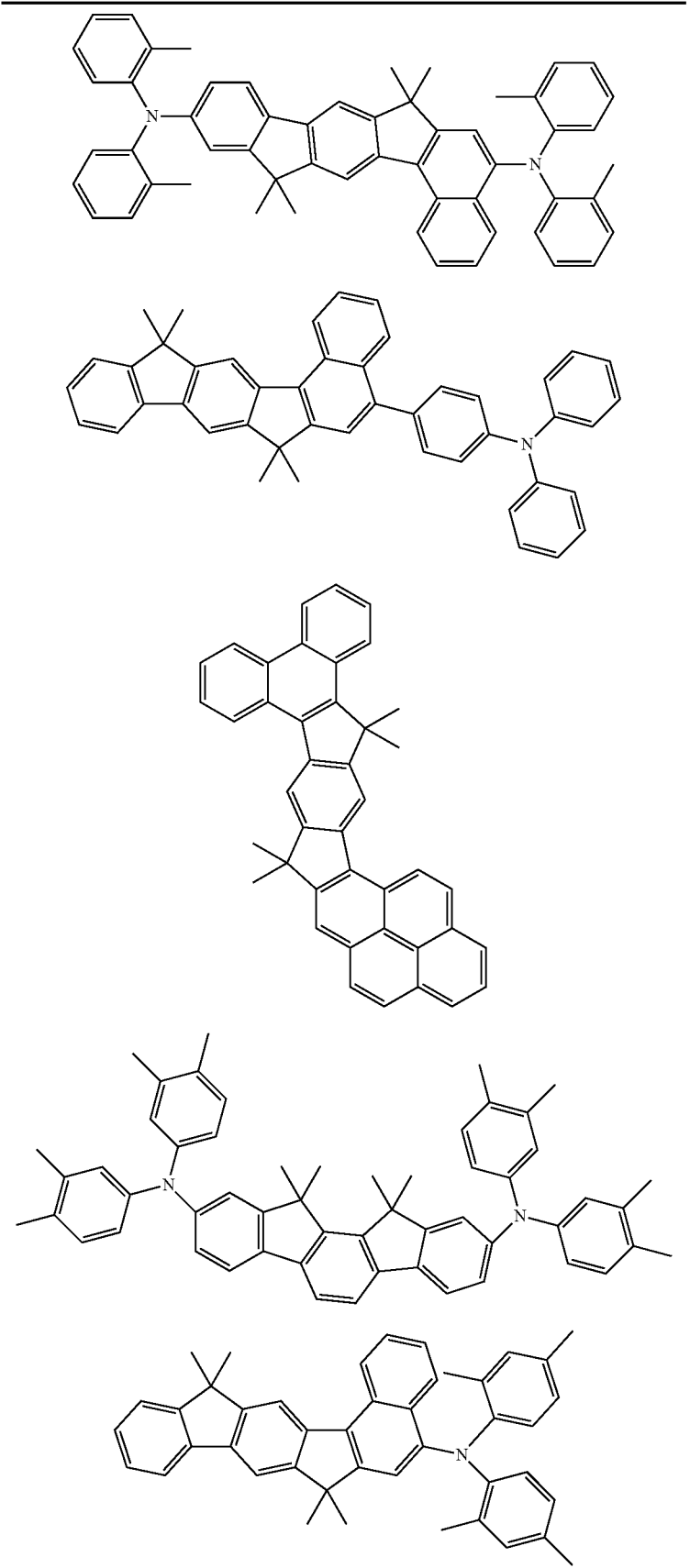

-continued
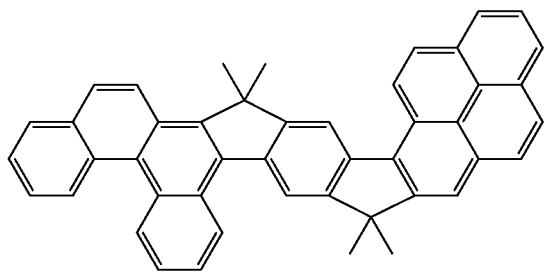 [SMILES: CC1(C)c2cc3c(cc2-c2c1cc1ccc4cccc5ccc2c1c45)C(C)(C)c1c-3c2ccccc2c2c1ccc1ccccc12]
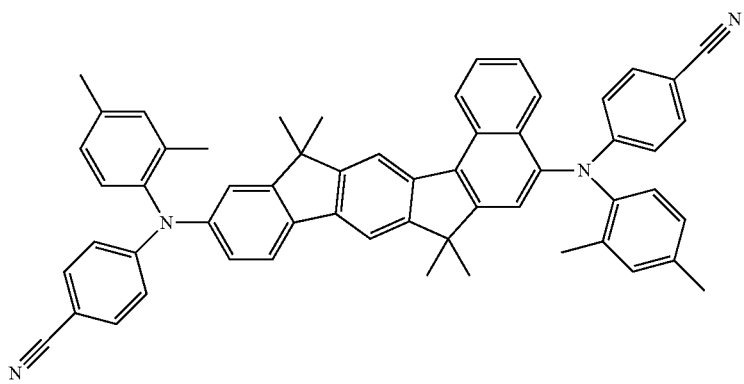 [SMILES: Cc1ccc(N(c2ccc(C#N)cc2)c2ccc3c(c2)C(C)(C)c2cc4c(cc2-3)C(C)(C)c2cc(N(c3ccc(C#N)cc3)c3ccc(C)cc3C)c3ccccc3c2-4)c(C)c1]
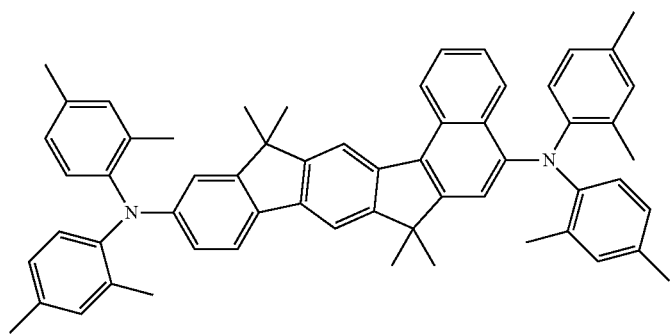
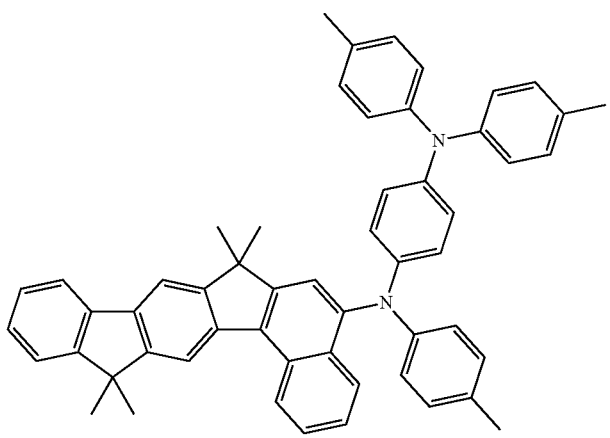 [SMILES: Cc1ccc(N(c2ccc(C)cc2)c2ccc(N(c3ccc(C)cc3)c3cc4c(c5ccccc35)-c3cc5c(cc3C4(C)C)-c3ccccc3C5(C)C)cc2)cc1]

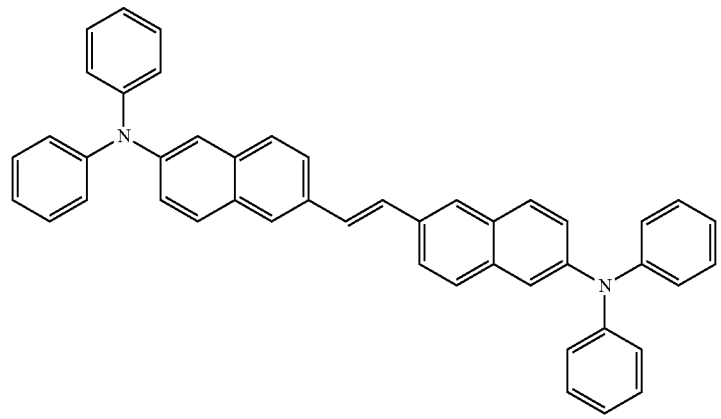 [SMILES: C(=C\c1ccc2cc(N(c3ccccc3)c3ccccc3)ccc2c1)/c1ccc2cc(N(c3ccccc3)c3ccccc3)ccc2c1]

Matrix materials which can be used, preferably for fluorescent dopants, are materials from various classes of substance. Preferred matrix materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 04/081017), the hole-conducting compounds (for example in accordance with WO 04/058911), the electron-conducting compounds, in particular ketones, phosphine oxides, sulfoxides, etc. (for example in accordance with WO 05/084081 and WO 05/084082), the atropisomers (for example in accordance with WO 06/048268), the boronic acid derivatives (for example in accordance with WO 06/117052) or the benzanthracenes (for example in accordance with WO 08/145239). Suitable matrix materials are furthermore preferably the compounds according to the invention. Apart from the compounds according to the invention, particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. For the purposes of this invention, an oligoarylene is intended to be taken to mean a compound in which at least three aryl or arylene groups are bonded to one another.

Suitable matrix materials, preferably for fluorescent dopants, are, for example, the materials depicted in the following table, and derivatives of these materials, as disclosed in WO 04/018587, WO 08/006449, U.S. Pat. No. 5,935,721, US 2005/0181232, JP 2000/273056, EP 681019, US 2004/0247937 and US 2005/0211958.

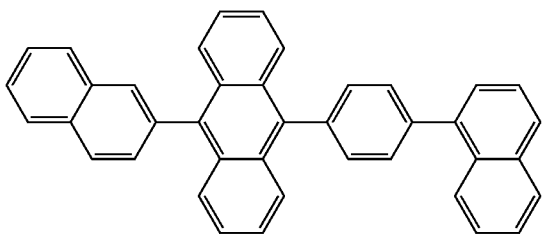 [SMILES: c1ccc2cc(-c3c4ccccc4c(-c4ccc(-c5cccc6ccccc56)cc4)c4ccccc34)ccc2c1]

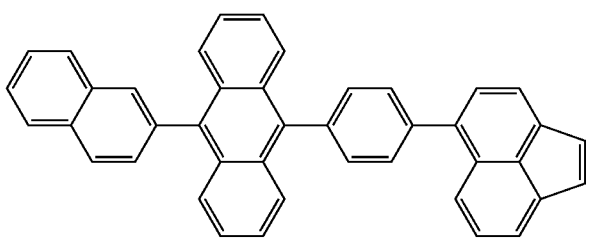 [SMILES: C1=Cc2ccc(-c3ccc(-c4c5ccccc5c(-c5ccc6ccccc6c5)c5ccccc45)cc3)c3cccc1c23]

-continued
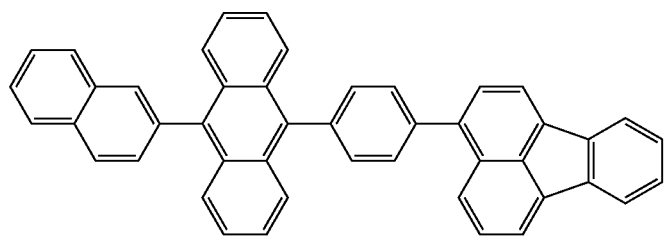 [SMILES: c1ccc2c(c1)-c1cccc3c(-c4ccc(-c5c6ccccc6c(-c6ccc7ccccc7c6)c6ccccc56)cc4)ccc-2c13]
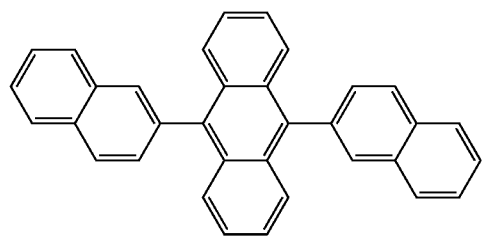 [SMILES: c1ccc2cc(-c3c4ccccc4c(-c4ccc5ccccc5c4)c4ccccc34)ccc2c1]
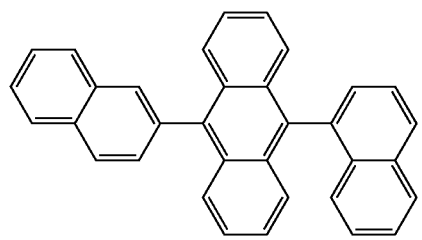 [SMILES: c1ccc2cc(-c3c4ccccc4c(-c4cccc5ccccc45)c4ccccc34)ccc2c1]
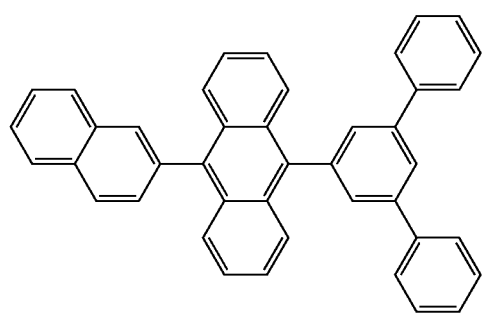 [SMILES: c1ccc(-c2cc(-c3ccccc3)cc(-c3c4ccccc4c(-c4ccc5ccccc5c4)c4ccccc34)c2)cc1]
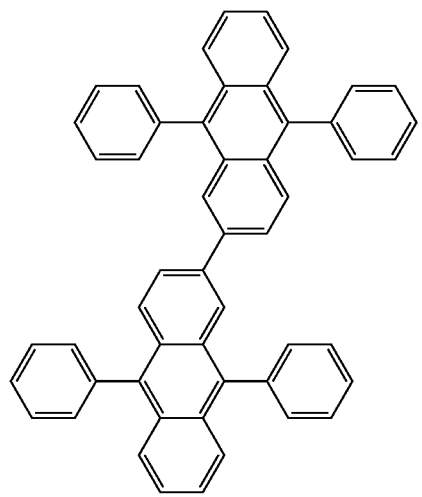 [SMILES: c1ccc(-c2c3ccccc3c(-c3ccccc3)c3cc(-c4ccc5c(-c6ccccc6)c6ccccc6c(-c6ccccc6)c5c4)ccc23)cc1]

-continued
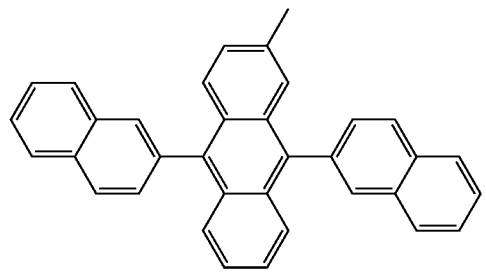 [SMILES: Cc1ccc2c(-c3ccc4ccccc4c3)c3ccccc3c(-c3ccc4ccccc4c3)c2c1]
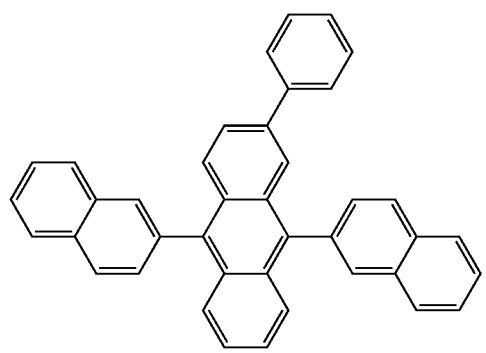 [SMILES: c1ccc(-c2ccc3c(-c4ccc5ccccc5c4)c4ccccc4c(-c4ccc5ccccc5c4)c3c2)cc1]
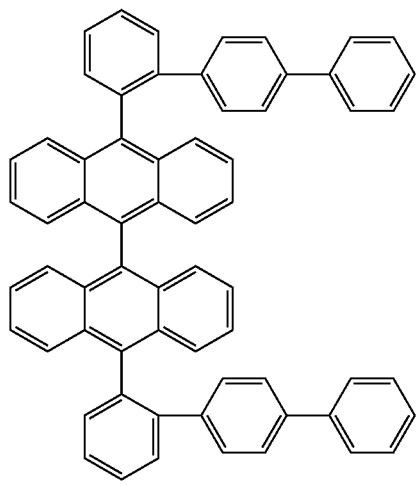 [SMILES: c1ccc(-c2ccc(-c3ccccc3-c3c4ccccc4c(-c4c5ccccc5c(-c5ccccc5-c5ccc(-c6ccccc6)cc5)c5ccccc45)c4ccccc34)cc2)cc1]
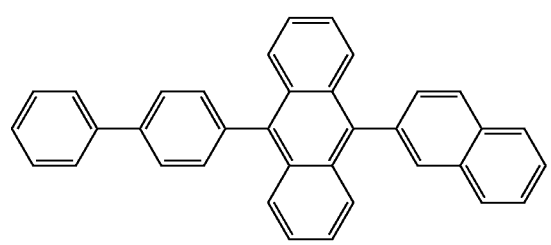 [SMILES: c1ccc(-c2ccc(-c3c4ccccc4c(-c4ccc5ccccc5c4)c4ccccc34)cc2)cc1]

-continued
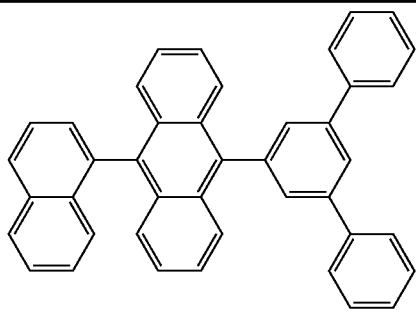
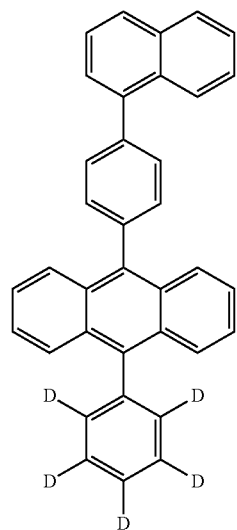 [SMILES: [2H]c1c([2H])c([2H])c(-c2c3ccccc3c(-c3ccc(-c4cccc5ccccc45)cc3)c3ccccc23)c([2H])c1[2H]]
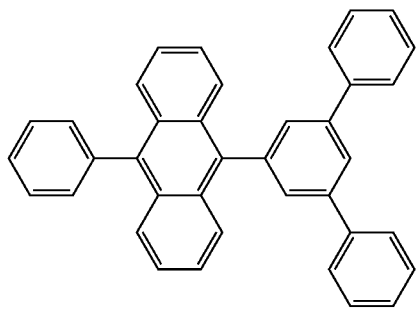 [SMILES: c1ccc(-c2cc(-c3ccccc3)cc(-c3c4ccccc4c(-c4ccccc4)c4ccccc34)c2)cc1]
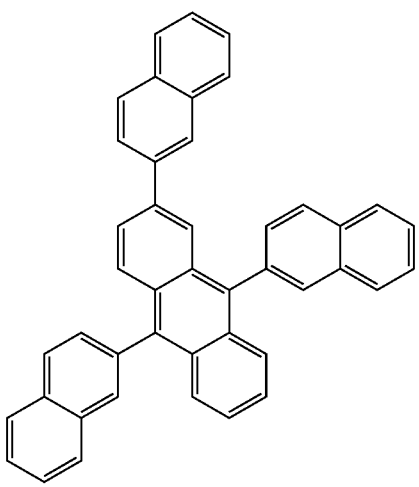 [SMILES: c1ccc2cc(-c3ccc4c(-c5ccc6ccccc6c5)c5ccccc5c(-c5ccc6ccccc6c5)c4c3)ccc2c1]

-continued
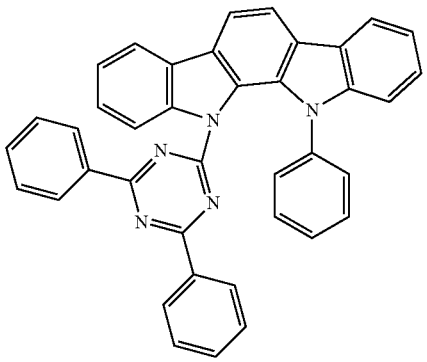 [SMILES: c1ccc(-c2nc(-c3ccccc3)nc(-n3c4ccccc4c4ccc5c6ccccc6n(-c6ccccc6)c5c43)n2)cc1]
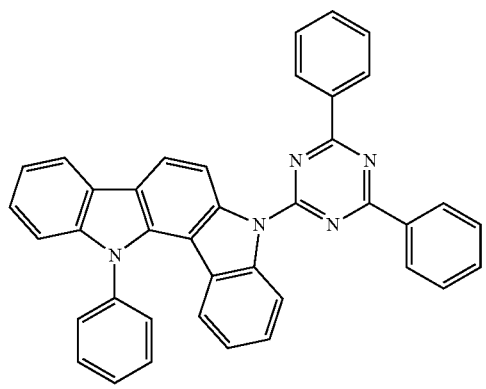 [SMILES: c1ccc(-c2nc(-c3ccccc3)nc(-n3c4ccccc4c4c3ccc3c5ccccc5n(-c5ccccc5)c34)n2)cc1]
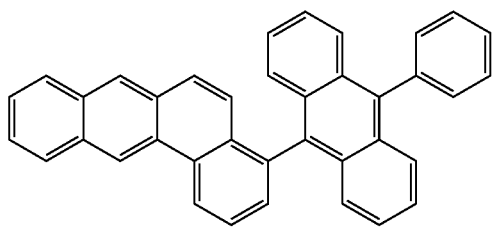 [SMILES: c1ccc(-c2c3ccccc3c(-c3cccc4c3ccc3cc5ccccc5cc34)c3ccccc23)cc1]
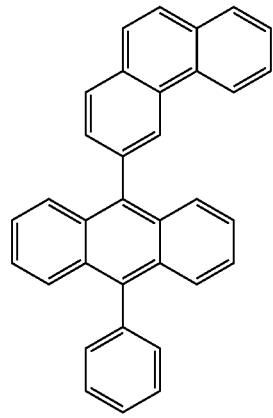 [SMILES: c1ccc(-c2c3ccccc3c(-c3ccc4ccc5ccccc5c4c3)c3ccccc23)cc1]

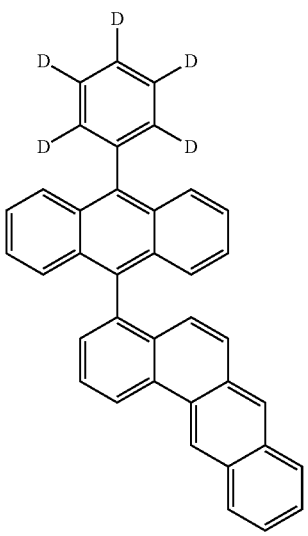 [SMILES: [2H]c1c([2H])c([2H])c(-c2c3ccccc3c(-c3cccc4c3ccc3cc5ccccc5cc34)c3ccccc23)c([2H])c1[2H]]
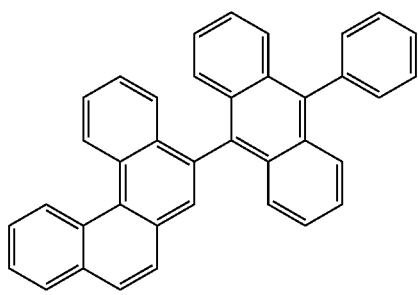 [SMILES: c1ccc(-c2c3ccccc3c(-c3cc4ccc5ccccc5c4c4ccccc34)c3ccccc23)cc1]
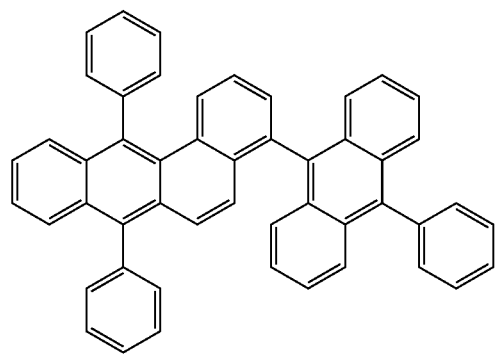 [SMILES: c1ccc(-c2c3ccccc3c(-c3cccc4c3ccc3c(-c5ccccc5)c5ccccc5c(-c5ccccc5)c34)c3ccccc23)cc1]
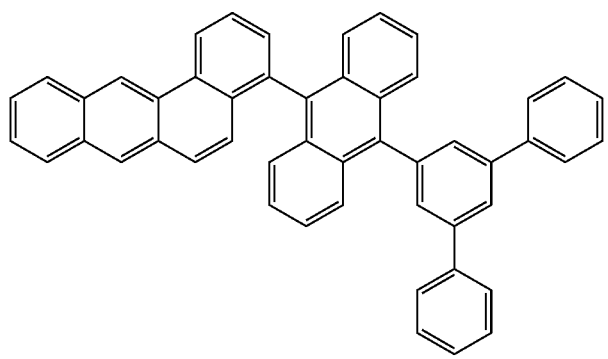 [SMILES: c1ccc(-c2cc(-c3ccccc3)cc(-c3c4ccccc4c(-c4cccc5c4ccc4cc6ccccc6cc45)c4ccccc34)c2)cc1]

-continued
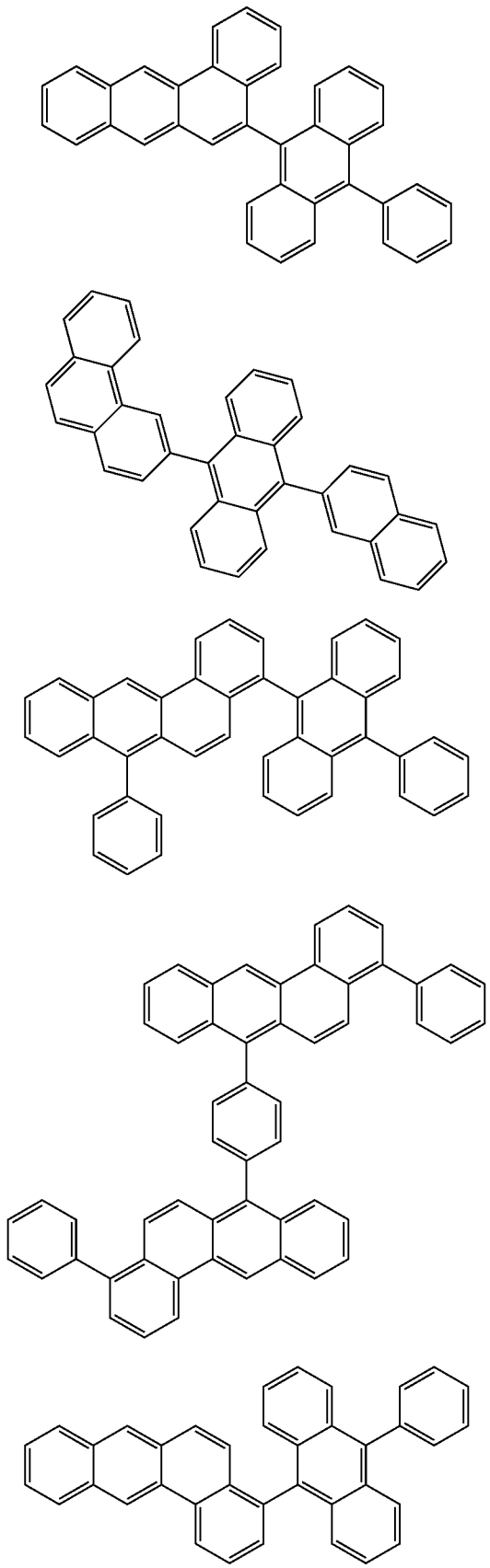

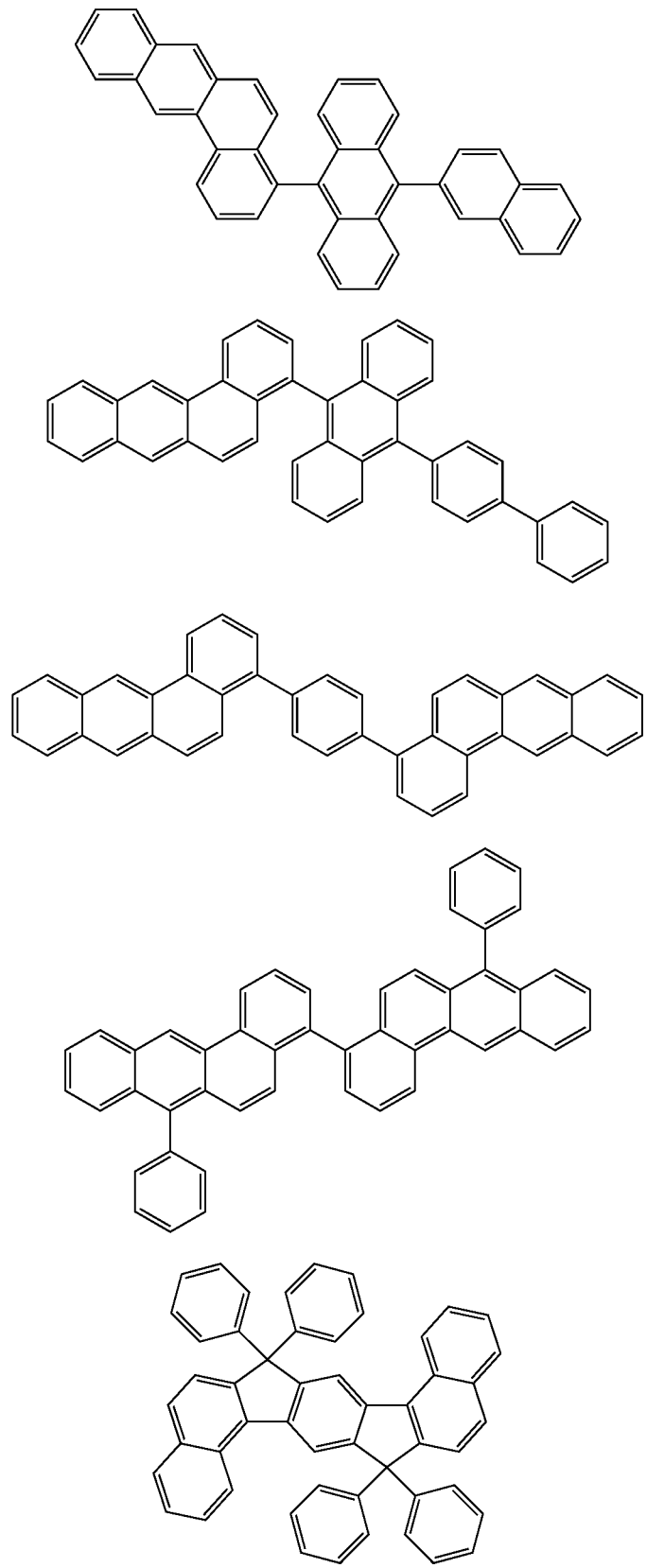

-continued
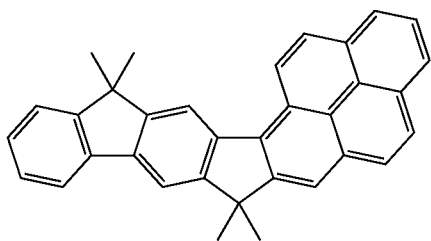 [SMILES: CC1(C)c2ccccc2-c2cc3c(cc21)-c1c(cc2ccc4cccc5ccc1c2c45)C3(C)C]
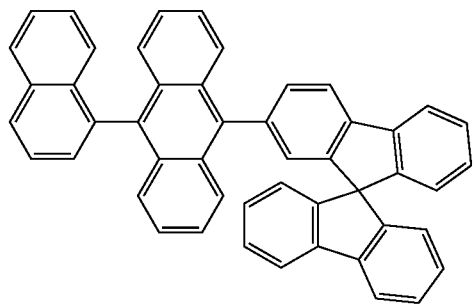 [SMILES: c1ccc2c(c1)-c1ccccc1C21c2ccccc2-c2ccc(-c3c4ccccc4c(-c4cccc5ccccc45)c4ccccc34)cc21]
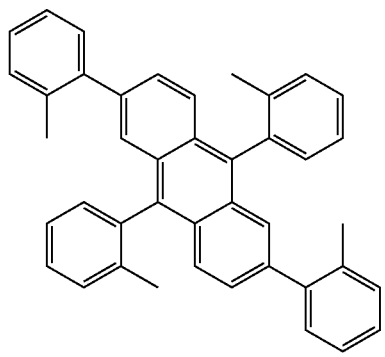 [SMILES: Cc1ccccc1-c1ccc2c(-c3ccccc3C)c3cc(-c4ccccc4C)ccc3c(-c3ccccc3C)c2c1]
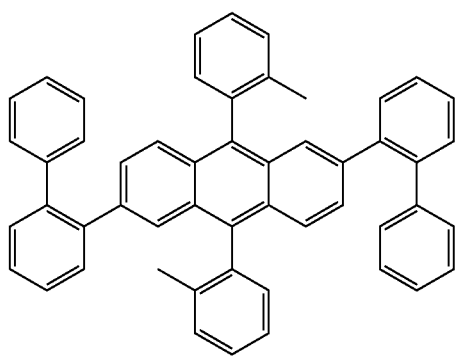 [SMILES: Cc1ccccc1-c1c2ccc(-c3ccccc3-c3ccccc3)cc2c(-c2ccccc2C)c2ccc(-c3ccccc3-c3ccccc3)cc12]
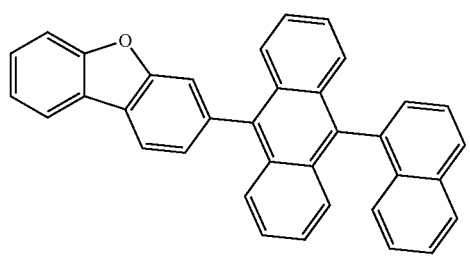 [SMILES: c1ccc2c(-c3c4ccccc4c(-c4ccc5c(c4)oc4ccccc45)c4ccccc34)cccc2c1]

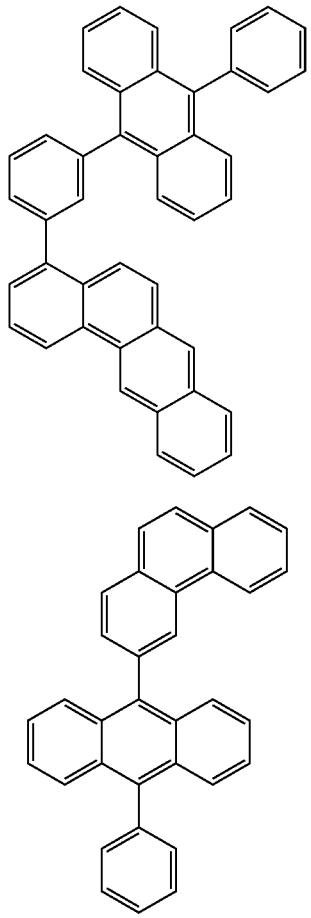

Besides the compounds according to the invention, suitable charge-transport materials, as can be used in the hole-injection or hole-transport layer or in the electron-transport layer of the organic electroluminescent device according to the invention, are, for example, the compounds disclosed in Y. Shirota et al., *Chem. Rev.* 2007, 107(4), 953-1010, or other materials as are employed in these layers in accordance with the prior art.

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ba/Ag, are then generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent or partially transparent in order to facilitate either irradiation of the organic material (organic solar cell) or the coupling-out of light (OLED, O-laser). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

Materials having a high glass transition temperature, high optical transparency and a high refractive index in the VIS region of the electromagnetic spectrum are used for the optional outcoupling layer. For example, oligoarylenes, arylamines or aromatic compounds which have been highly functionalised in another manner can be used in the outcoupling layer.

The device is appropriately (depending on the application) structured, provided with contacts and finally sealed, since the lifetime of the devices according to the invention is shortened in the presence of water and/or air.

In a preferred embodiment, the organic electroluminescent device according to the invention is characterised in that one or more layers are applied by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., Appl. Phys. Lett. 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I) are necessary for this purpose. High solubility can be achieved through suitable substitution of the compounds.

It is furthermore preferred to produce an organic electroluminescent device according to the invention by applying one or more layers from solution and one or more layers by a sublimation process.

In accordance with the invention, the electronic devices comprising one or more compounds of the formula (I) can be employed in displays, as light sources in lighting applications and as light sources in medical and/or cosmetic applications (for example in light therapy).

The compounds according to the invention preferably have one or more of the following advantages over the prior art on use in organic electroluminescent devices:

1. The compounds have a high glass transition temperature, which is preferably above 100° C. A high glass transition temperature typically correlates with good film-formation properties, which are highly desired for materials for use in OLEDs.
2. The compounds can easily be sublimed and exhibit no or only slight decomposition on sublimation. This simplifies purification of the compounds and thus the achievement of a high degree of purity in the compounds.
3. The compounds have good charge-transport properties. This causes the operating voltage to be virtually independent of the layer thickness of the corresponding hole-transport or hole-injection layer.

The present application text and also the following examples are directed to the use of the compounds according to the invention in relation to OLEDs and the corresponding displays. In spite of this restriction of the description, it is possible for the person skilled in the art, without further inventive step, also to employ the compounds according to the invention for further uses in other electronic devices, for example for organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic photoreceptors or also organic laser diodes (O-lasers), to mention but a few applications. Of these, preference is given to the use in organic solar cells and/or organic integrated circuits.

The present invention likewise relates to the use of the compounds according to the invention in the corresponding devices and to these devices themselves.

The invention is explained in greater detail by the following examples without wishing to restrict it thereby.

WORKING EXAMPLES

I. Synthesis Examples

The following syntheses are carried out under a protective-gas atmosphere, unless indicated otherwise. The starting materials are purchased from ALDRICH or ABCR, unless mentioned otherwise.

Example 1

Synthesis of N,N,N',N'-tetra-p-tolyl-9,9'-spirobifluorene-2,7-diamine (HTM1)

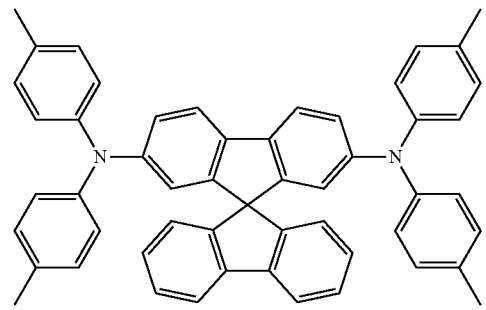 [SMILES: Cc1ccc(N(c2ccc(C)cc2)c2ccc3c(c2)C2(c4ccccc4-c4ccccc42)c2cc(N(c4ccc(C)cc4)c4ccc(C)cc4)ccc2-3)cc1]

100 g (211 mmol) of 2,7-dibromospirobifluorene (Beijing Aglaia Techn. Dev. Co. Ltd.) and 60.8 g (633 mmol) of NaOtBu in 1.5 l of abs. toluene are initially introduced under $N_2$ into a 4 l four-necked flask with internal thermometer, precision-glass stirrer and reflux condenser and degassed for 30 minutes by passing-through of $N_2$. 1.65 ml (8.7 mmol) of di-t-butyl-chlorophosphine and 1.15 g (1.5 mmol) of palladium acetate are subsequently added. 104.1 g (527 mmol) of di-p-tolylamine are then added, and the mixture is heated under reflux for 12 h. 100 ml of acetic acid are added dropwise to the cooled batch, and 500 ml of ethanol and a further 100 ml of acetic acid are then added. The precipitated solid is filtered off with suction via a frit and dried at 40° C. in vacuo.

The resultant solid is recrystallised 5× from dioxane and sublimed in vacuo ($10^{-5}$ mbar, 340° C.), giving 63 g (89 mmol, 42%) of N,N,N',N'-tetra-p-tolyl-9,9'-spirobifluorene-2,7-diamine (HTM1) as a colourless solid. Analytical data: Tg (DSC) 123° C., purity >99.98%.

Example 2

Synthesis of N,N,N',N'-tetrakis(2,4-dimethylphenyl)-9,9'-spiro-bifluorene-2,7-diamine (HTM2)

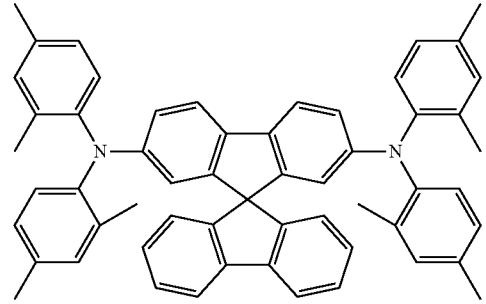 [SMILES: Cc1ccc(N(c2ccc3c(c2)C2(c4ccccc4-c4ccccc42)c2cc(N(c4ccc(C)cc4C)c4ccc(C)cc4C)ccc2-3)c2ccc(C)cc2C)c(C)c1]

The synthesis is carried out analogously to Example 1, with the difference that 118.7 g of di(2,4-dimethylphenyl)amine (Wie-Flex Technology) are employed instead of the di-p-tolylamine. After crystallisation six times from dioxane and sublimation ($10^{-5}$ mbar, 350° C.), 72 g (93 mmol, 45%) of N,N,N',N'-tetrakis(2,4-dimethylphenyl)-9,9'-spirobifluorene-2,7-diamine (HTM2) are obtained as a colourless solid. Analytical data: Tg (DSC) 128° C., purity >99.98%.

Example 3

Synthesis of N,N,N',N'-tetrakis(3-methylphenyl)-2',7'-diphenyl-9,9'-spirobifluorene-2,7-diamine (HTM3)

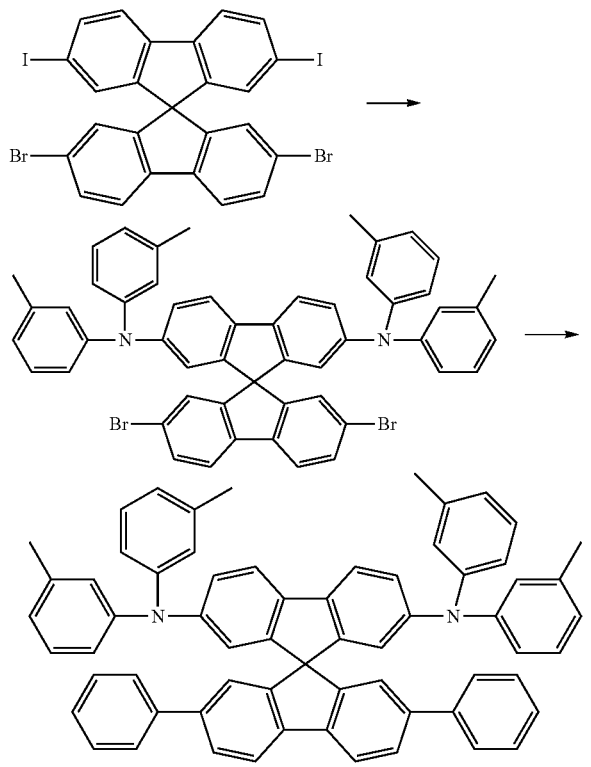

The synthesis of the starting material 2,7-diiodo-2',7'-dibromo-9,9'-spirobifluorene is described in the application WO 2003/020790.

Step a: The synthesis is carried out analogously to Example 1, with the difference that 104.1 g (527 mmol) of di(3-methylphenyl)amine are employed instead of the di-p-tolylamine and 153.1 g (211 mmol) of 2,7-diiodo-2',7'-dibromo-9,9'-spirobifluorene are employed instead of the dibromospirobifluorene. After crystallisation from dioxane and sublimation, 134.5 g (190 mmol, 90%) of N,N,N',N'-tetrakis(3-methylphenyl)-2',7'-dibromo-9,9'-spirobifluorene-2,7-diamine are obtained as a colourless solid.

Step b: 134.5 g (190 mmol) of N,N,N',N'-tetrakis(3-methylphenyl)-2',7'-dibromo-9,9'-spirobifluorene-2,7-diamine, 50.4 g (420 mmol) of benzene-boronic acid and potassium phosphate (195.5 g, 0.92 mol) are initially introduced into a 4 l flask, and 1200 ml of toluene, 1200 ml of water and 475 ml of dioxane are then added. The mixture is degassed for 30 minutes by passing-through of argon with stirring. The tris-o-tolylphosphine (4.0 g, 13.2 mmol) is then added, and the mixture is stirred briefly. Palladium(II) acetate (480 mg, 2.1 mmol) is subsequently added. Finally, the mixture is heated under reflux for 12 hours. A further 10 g of boronic acid ester are added, and the mixture is heated under reflux for a further 10 h. The mixture is then allowed to cool. Glacial acetic acid/ethanol 1:1 (1500 ml) is subsequently added. The precipitated solid is filtered off with suction, rinsed 2× with about 250 ml of toluene, 2× with about 450 ml of water/ethanol mixture (ratio 1:1) and finally 2× with 550 ml of ethanol. The solid is extracted with 2 l of toluene in a hot extractor for 5 days and subsequently recrystallised 4× from degassed dioxane. The product is sublimed at 5× $10^{-6}$ mbar and about 330° C.

Yield: 79.9 g (49% of theory); analytical data: Tg (DSC) 146° C., purity >99.98%.

Example 4

Synthesis of N,N,N',N'-tetrakis(3,4-dimethylphenyl)-9,9'-spirobifluorene-2,7-diamine (HTM4)

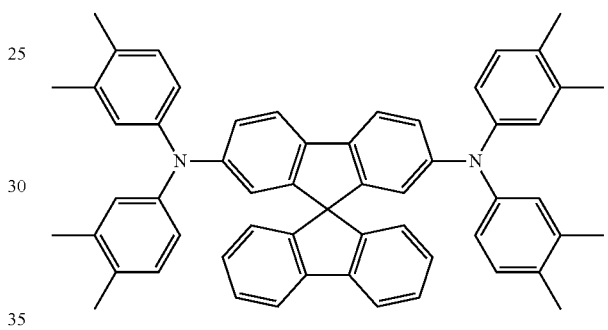

The synthesis is carried out analogously to Example 1, with the difference that 118.7 g of di(3,4-dimethylphenyl)amine (Wie-Flex Technology) are employed instead of the di-p-tolylamine. After crystallisation four times from dioxane and sublimation ($10^{-5}$ mbar, 345° C.), 70 g (90 mmol, 43%) of N,N,N',N'-tetrakis(3,4-dimethylphenyl)-9,9'-spirobifluorene-2,7-diamine (HTM4) are obtained as a colourless solid. Analytical data: Tg (DSC) 133° C., purity (HPLC) >99.98%.

Comparative Example C1

Synthesis of N,N,N',N'-tetrakisphenyl-9,9'-spirobifluorene-2,7-diamine (HTMC1)

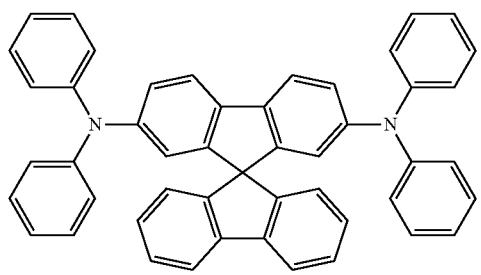 [SMILES: c1ccc(N(c2ccccc2)c2ccc3c(c2)C2(c4ccccc4-c4ccccc42)c2cc(N(c4ccccc4)c4ccccc4)ccc2-3)cc1]

The synthesis is carried out analogously to Example 1, with the difference that 89.2 g of diphenylamine are employed instead of the di-p-tolylamine. After crystallisation six times from toluene and sublimation ($10^{-5}$ mbar, 320° C.), 53.5 g (82 mmol, 39%) of N,N,N',N'-tetraphenyl-9,9'-spirobifluorene-2,7-diamine (HTMC1) are obtained as a colourless solid. Analytical data: Tg (DSC) 112° C., purity (HPLC) >99.98%.

Comparative Example C2

Synthesis of N,N'-bis(3-methylphenyl)-N,N'-diphenyl-9,9-spirobifluorene-2,7-diamine (HTMC2)

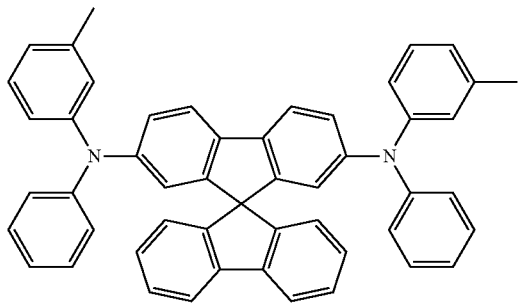 [SMILES: Cc1cccc(N(c2ccccc2)c2ccc3c(c2)C2(c4ccccc4-c4ccccc42)c2cc(N(c4ccccc4)c4cccc(C)c4)ccc2-3)c1]

The synthesis is carried out analogously to Example 1, with the difference that 96.6 g of (m-methylphenyl)phenylamine are employed instead of the di-p-tolylamine. After crystallisation ten times from toluene and sublimation ($10^{-5}$ mbar, 320° C.), 50.1 g (74 mmol, 35%) of N,N'-bis(3-methylphenyl)-N,N'-diphenyl-9,9-spirobifluorene-2,7-diamine (HTMC2) are obtained as a colourless solid. Analytical data: Tg (DSC) 102° C., purity (HPLC) 99.98%.

Comparative Example C3

Synthesis of N,N,N',N',N'',N'',N''',N'''-octakisphenyl-9,9'-spirobifluorene-2,2',7,7'-diamine (HTMC3)

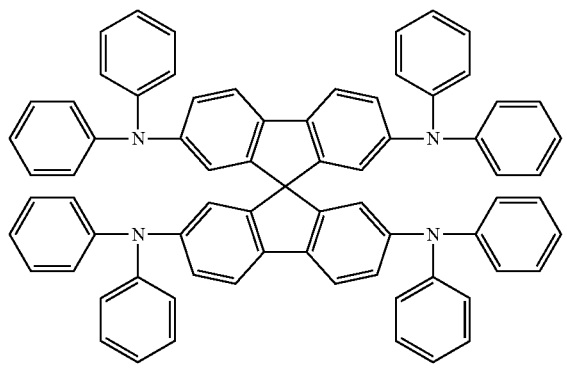 [SMILES: c1ccc(N(c2ccccc2)c2ccc3c(c2)C2(c4cc(N(c5ccccc5)c5ccccc5)ccc4-3)c3cc(N(c4ccccc4)c4ccccc4)ccc3-c3ccc(N(c4ccccc4)c4ccccc4)cc32)cc1]

The synthesis is carried out as described in EP 1442007 (Example 1). In order to obtain a purity of >99.98%, the product is recrystallised 6 times and subsequently sublimed 2× (405° C.; $5*10^{-5}$ mbar). Tg (DSC) 135° C., purity (HPLC) >99.98%.

Comparative Example C4

Synthesis of N,N'-diphenyl-N,N'-bis(5,6,7,8-tetrahydro-1-naphthyl)-9,9-spirobifluorene-2,7-diamine (HTMC4)

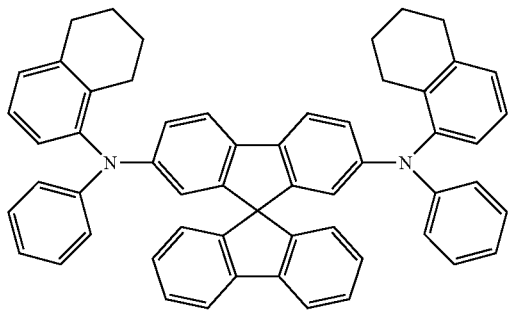 [SMILES: c1ccc(N(c2ccc3c(c2)C2(c4ccccc4-c4ccccc42)c2cc(N(c4ccccc4)c4cccc5c4CCCC5)ccc2-3)c2cccc3c2CCCC3)cc1]

The synthesis is carried out as described in U.S. Pat. No. 7,273,953 (Example 17; compound 1-15). In order to obtain a purity of >99.98%, the product is recrystallised 6 times and subsequently sublimed 2× (330° C.; $2*10^{-5}$ mbar). Tg (DSC) 121° C., purity (HPLC) >99.98%.

II. Investigations of the Thermal Stability of the Materials

The following compounds are investigated with respect to their vapour-deposition behaviour (i.e. temperature) in OLED manufacture. The materials are subsequently investigated in a so-called temper test for their stability at the corresponding temperature. The following procedure is followed here:
a) The temperature at which the corresponding material is vapour-deposited at a rate of 0.2 nm/s in the research evaporator (Lesker, model TUR-035) is determined.
b) A material sample (100 mg) is then melt-sealed into a quartz ampoule in vacuo and stored for 7 days (in a muffle furnace) at a temperature which is at least 50° C. above the temperature determined under a). This increase by at least 50° C. corresponds to an empirical experience value: it is approximately the increase to be expected on transfer to standard production units (for example Tokki).
c) After the 7 days, the ampoule is cooled, opened and the material inside is investigated for purity (by HPLC and H-NMR).

The results obtained are summarised in the following table:

| Material | Temperature in Lesker unit [° C.] | Temperature in temper test [° C.] | Purity before temper test | Purity after temper test |
|---|---|---|---|---|
| HTM1 | 180 | 240 | >99.98% | >99.98% |
| HTM2 | 170 | 240 | >99.98% | >99.98% |
| HTM3 | 225 | 280 | >99.98% | >99.98% |
| HTM4 | 180 | 240 | >99.98% | >99.98% |
| HTMC1 | 165 | 220 | >99.98% | >99.98% |
| HTMC2 | 170 | 220 | ~99.98% | ~99.98% |
| HTMC3 | 285 | 340 | >99.98% | ~99.53% |

The investigation shows that the materials according to the invention have increased thermal stability at application-relevant temperatures compared with the corresponding tetraamino-substituted spirobifluorenes, such as HTMC3.

III. Formation and Stability of Amorphous Films

Two quartz plates are coated with 100 nm thick films of each of the following compounds by vacuum evaporation (Lesker research evaporator, see above). These plates are transferred into an argon-filled glove box, where they are investigated for appearance and transparency.

The films are then stored in this glove box at two different temperatures for 4 weeks and re-assessed.

The results of the investigations are summarised in the following table:

| Material | Film property immediately after vapour deposition | Film property after 4 weeks at 22° C. | Film property after 4 weeks at 65° C. |
|---|---|---|---|
| HTM1 | +++ | +++ | ++ |
| HTM2 | +++ | +++ | ++ |
| HTM3 | +++ | +++ | +++ |
| HTM4 | +++ | +++ | +++ |
| HTMC1 | ++ | 0 | -- |
| HTMC2 | +++ | ++ | 0 |
| HTMC3 | +++ | +++ | +++ |

Assessment of the film properties by visual inspection and taking of a photo-micrograph:
+++ = clear transparent film, no defects;
++ = clear transparent film, few small defects;
+ = transparent film, many small defects;
0 = transparent film, with clearly visible crystallites;
− = slightly hazy film;
−− = hazy film;
−−− = very hazy film or fully crystallised segments.

The investigation shows that the materials according to the invention have improved film-formation properties and film stabilities compared with the corresponding unsubstituted or lower alkyl-substituted comparative compounds (HTMC1 and HTMC2).

IV. Stability of Solutions

In order to investigate whether the materials are also suitable for use in printing processes, the materials are dissolved in organic solvents. The dissolution is carried out in nitrogen-saturated solvents by stirring the corresponding materials at 60° C. for 6 h. After cooling, the solutions are investigated. For storage tests, the solutions are transferred into glass bottles (clean room, air) and stored in a solvent cabinet at 25° C. After 4 weeks, the solutions are re-investigated. The solutions are investigated for concentration, any crystallisation and for potential decomposition of the compound (to this end, a sample is in each case freed from solvent in vacuo and investigated for purity by H-NMR and HPLC).

| Material | Solvent | Immediately after dissolution | | | After storage for 4 weeks | | |
|---|---|---|---|---|---|---|---|
| | | Conc. [g/l] | Purity [%] | Precipitate? | Conc. [g/l] | Purity [%] | Precipitate? |
| HTM1 | Anisole | 15 | 99.98 | no | 15 | 99.98 | no |
| HTM2 | Anisole | 20 | 99.98 | no | 20 | 99.98 | no |
| HTM3 | 4-Methyl-anisole | 15 | 99.98 | no | 15 | 99.98 | no |
| HTM4 | 4-Methyl-anisole | 20 | 99.98 | no | 20 | 99.98 | no |
| HTMC1 | 4-Methyl-anisole | 15 | 99.98 | no | 13 | 99.98 | yes |
| HTMC3 | 4-Methyl-anisole | 12 | 99.98 | no | ~10 | 99.98 | yes |
| HTMC4 | Anisole | 20 | 99.98 | no | 20 | 98.68*) | no |

*) The H-NMR shows signals which indicate peroxide formation in the tetralin ring The investigation shows that the materials according to the invention have improved properties with respect to solution stability, in particular less crystallisation and chemical degradation.

V. Device Examples

OLEDs according to the invention and OLEDs in accordance with the prior art are produced by a general process in accordance with WO 04/058911, which is adapted to the circumstances described here (layer-thickness variation, materials used).

The results for various OLEDs are presented in the following examples. Glass plates coated with structured ITO (indium tin oxide) in a thickness of 50 nm form the substrates, to which the OLEDs are applied. The OLEDs have in principle the following layer structure: substrate/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is shown in Table 1. The materials used for the production of the OLEDs are shown in Table 3.

All materials are applied by thermal vapour deposition in a vacuum chamber. The emission layer here always consists of at least one matrix material (host material) and an emitting dopant (emitter), which is admixed with the matrix material or materials in a certain proportion by volume by co-evaporation. Information such as H1:SEB1 (95%:5%) here means that material H1 is present in the layer in a proportion by volume of 95% and SEB1 is present in the layer in a proportion by volume of 5%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current-voltage-luminance characteristic lines (IUL characteristic lines), and the lifetime are determined. The lifetime is defined as the time after which the luminous density has dropped to a certain proportion from a particular initial luminous density $I_0$. The designation LD50 means that the said lifetime is the time at which the luminous density has dropped to $0.5 \cdot I_0$ (to 50%), i.e. from, for example, 6000 cd/m² to 3000 cd/m².

The compounds according to the invention can be employed, inter alia, as hole-injecting and hole-transporting materials. Compounds HTM1 to HTM4 according to the invention are used here. Compounds HTMC2 and HTMC3 are used as comparative compounds in accordance with the prior art. OLEDs comprising the blue-emitting dopant SEB1 are shown. The performance data obtained for the OLEDs are summarised in Table 2. Experiments called O-C1 to O-C6 are carried out using HTMC materials and serve as comparative examples: OLEDs O-1 to O-10 according to the invention are produced using materials according to the invention.

TABLE 1

| Ex. | HTL Thickness/nm | IL Thickness/nm | EBL Thickness/nm | EML Thickness/nm | ETL Thickness/nm | EIL Thickness/nm |
|---|---|---|---|---|---|---|
| O-C1 | HTMC3 40 nm | HIL1 5 nm | NPB 25 nm | H1(95%):SEB1(5%) 25 nm | ETM1(50%):LiQ(50%) 25 nm | |
| O-C2 | HTMC3 40 nm | HIL1 5 nm | NPB 25 nm | H1(95%):SEB1(5%) 25 nm | ETM1(25%):LiQ(70%) 25 nm | |
| O-C3 | HTMC3 40 nm | HIL1 5 nm | NPB 25 nm | H1(95%):SEB1(5%) 25 nm | ETM1 25 nm | LiQ 3 nm |
| O-C4 | HTMC3 40 nm | HIL1 5 nm | NPB 25 nm | H1(95%):SEB1(5%) 25 nm | Alq 25 nm | LiF 1 nm |
| O-C5 | HTMC2 40 nm | HIL1 5 nm | NPB 25 nm | H1(95%):SEB1(5%) 25 nm | ETM1 25 nm | LiQ 3 nm |
| O-C6 | HTMC2 40 nm | HIL1 5 nm | NPB 25 nm | H1(95%):SEB1(5%) 25 nm | Alq 25 nm | LiF 1 nm |
| O-1 | HTM1 40 nm | HIL1 5 nm | NPB 25 nm | H1(95%):SEB1(5%) 25 nm | ETM1(50%):LiQ(50%) 25 nm | |
| O-2 | HTM1 40 nm | HIL1 5 nm | NPB 25 nm | H1(95%):SEB1(5%) 25 nm | ETM1(25%):LiQ(70%) 25 nm | |
| O-3 | HTM1 40 nm | HIL1 5 nm | NPB 25 nm | H1(95%):SEB1(5%) 25 nm | ETM1 25 nm | LiQ 3 nm |
| O-4 | HTM1 40 nm | HIL1 5 nm | NPB 25 nm | H1(95%):SEB1(5%) 25 nm | Alq 25 nm | LiF 1 nm |
| O-5 | HTM2 40 nm | HIL1 5 nm | NPB 25 nm | H1(95%):SEB1(5%) 25 nm | ETM1(50%):LiQ(50%) 25 nm | |
| O-6 | HTM2 40 nm | HIL1 5 nm | NPB 25 nm | H1(95%):SEB1(5%) 25 nm | ETM1(25%):LiQ(70%) 25 nm | |
| O-7 | HTM3 40 nm | HIL1 5 nm | NPB 25 nm | H1(95%):SEB1(5%) 25 nm | ETM1(50%):LiQ(50%) 25 nm | |
| O-8 | HTM3 40 nm | HIL1 5 nm | NPB 25 nm | H1(95%):SEB1(5%) 25 nm | ETM1(25%):LiQ(70%) 25 nm | |
| O-9 | HTM4 40 nm | HIL1 5 nm | NPB 25 nm | H1(95%):SEB1(5%) 25 nm | ETM1(50%):LiQ(50%) 25 nm | |
| O-10 | HTM4 40 nm | HIL1 5 nm | NPB 25 nm | H1(95%):SEB1(5%) 25 nm | ETM1(25%):LiQ(70%) 25 nm | |

TABLE 2

| Ex. | Efficiency @ 1000 cd/m² [cd/A] | Voltage @ 1000 cd/m² [V] | CIE @ 1000 cd/m² x | CIE @ 1000 cd/m² y | LD50 @ 6000 cd/m² [h] |
|---|---|---|---|---|---|
| O-C1 | 7.3 | 3.7 | 0.142 | 0.145 | 230 |
| O-C2 | 7.0 | 4.0 | 0.141 | 0.146 | 450 |
| O-C3 | 8.7 | 3.2 | 0.142 | 0.148 | 120 |
| O-C4 | 4.3 | 5.4 | 0.153 | 0.160 | 390 |
| O-C5 | 8.7 | 3.3 | 0.141 | 0.146 | 125 |
| O-C6 | 4.2 | 5.6 | 0.155 | 0.160 | 370 |
| O-1 | 7.4 | 3.7 | 0.142 | 0.148 | 240 |
| O-2 | 7.0 | 3.9 | 0.140 | 0.144 | 470 |
| O-3 | 8.6 | 3.1 | 0.140 | 0.147 | 130 |
| O-4 | 4.3 | 5.5 | 0.155 | 0.158 | 410 |
| O-5 | 7.3 | 3.7 | 0.141 | 0.146 | 230 |
| O-6 | 7.0 | 4.0 | 0.142 | 0.144 | 440 |
| O-7 | 7.2 | 3.8 | 0.143 | 0.143 | 240 |
| O-8 | 7.1 | 4.1 | 0.139 | 0.147 | 470 |
| O-9 | 7.3 | 3.7 | 0.141 | 0.148 | 240 |
| O-10 | 7.0 | 4.0 | 0.143 | 0.144 | 430 |

TABLE 3

Alq₃

LiQ

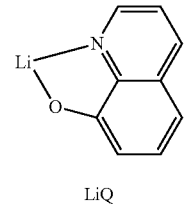

NPB

TABLE 3-continued
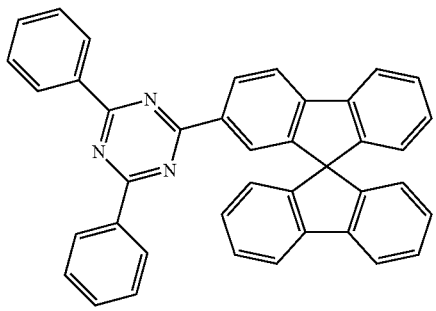 [SMILES: c1ccc(-c2nc(-c3ccccc3)nc(-c3ccc4c(c3)C3(c5ccccc5-c5ccccc53)c3ccccc3-4)n2)cc1]
ETM1
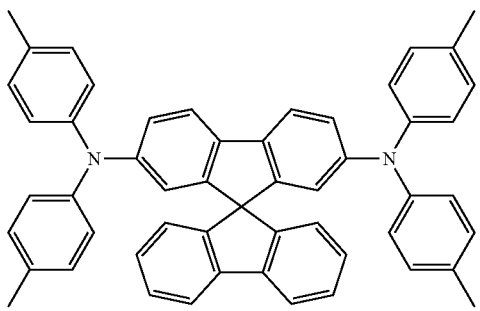
HTM1
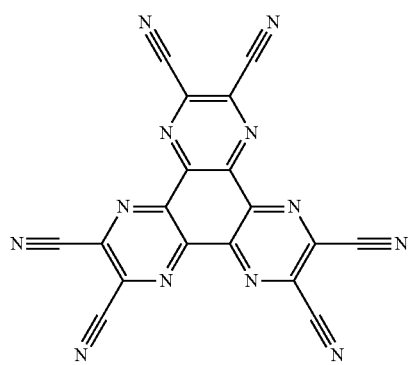 [SMILES: N#Cc1nc2c3nc(C#N)c(C#N)nc3c3nc(C#N)c(C#N)nc3c2nc1C#N]
HIL1
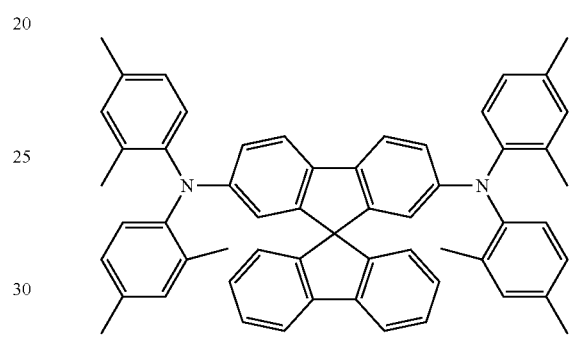
HTM2
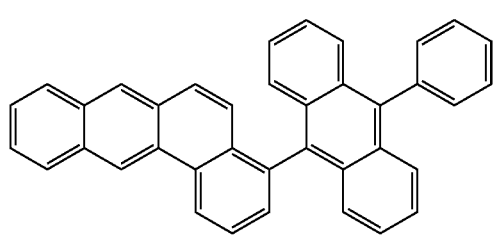 [SMILES: c1ccc(-c2c3ccccc3c(-c3cccc4c3ccc3cc5ccccc5cc34)c3ccccc23)cc1]
H1
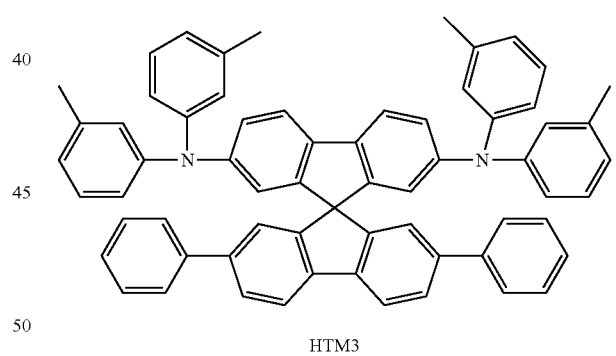
HTM3
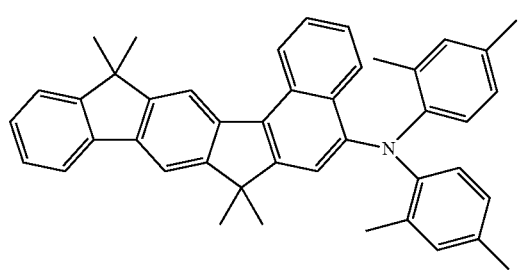 [SMILES: Cc1ccc(N(c2ccc(C)cc2C)c2cc3c(c4ccccc24)-c2cc4c(cc2C3(C)C)-c2ccccc2C4(C)C)c(C)c1]
SEB1
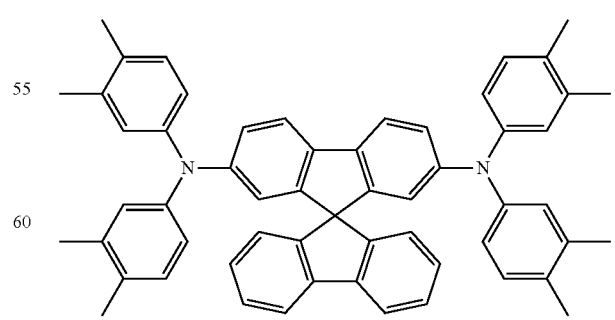
HTM4

TABLE 3-continued

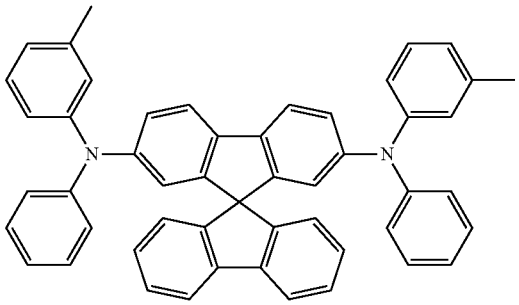 [SMILES: Cc1cccc(N(c2ccccc2)c2ccc3c(c2)C2(c4ccccc4-c4ccccc42)c2cc(N(c4ccccc4)c4cccc(C)c4)ccc2-3)c1]

HTMC2

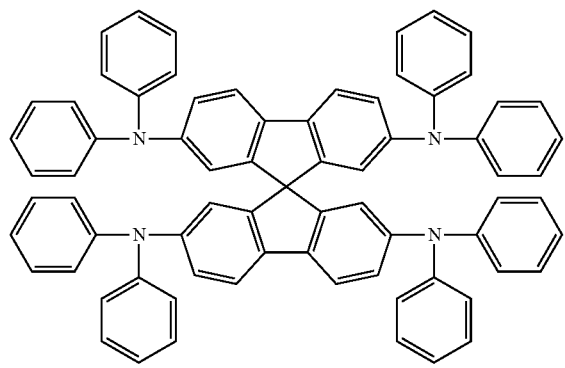 [SMILES: c1ccc(N(c2ccccc2)c2ccc3c(c2)C2(c4cc(N(c5ccccc5)c5ccccc5)ccc4-3)c3cc(N(c4ccccc4)c4ccccc4)ccc3-c3ccc(N(c4ccccc4)c4ccccc4)cc32)cc1]

HTMC3

The examples shown confirm that the materials according to the invention are highly suitable for use as hole-injection materials or hole-transport materials in electronic devices. The performance data obtained confirm that similarly good or improved results are obtained thereby compared with the prior art.

The invention claimed is:

1. An electroluminescent device comprising a hole-transport material, matrix material, or emitter material, the material including at least one compound of formula (I), formula (I)

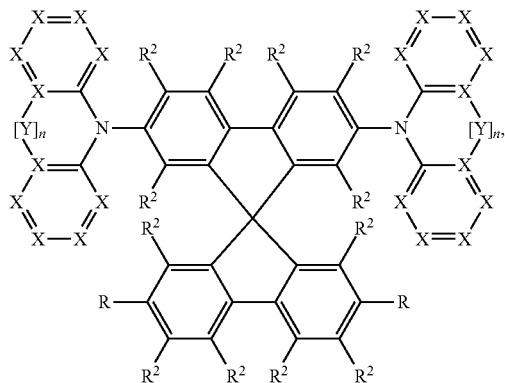

wherein:
X is, identically or differently on each occurrence, CH or $CR^1$, with the provisos that at least two groups X per aromatic 6-membered ring is $CR^1$, and X is C when Y is bonded to X;
Y is, identically or differently on each occurrence, a single bond, O, S, $C(R^3)_2$, or $NR^3$;
R is, identically or differently on each occurrence, H, D, CHO, $C(=O)R^3$, $P(=O)(R^3)_2$, $S(=O)R^3$, $S(=O)_2R^3$, CN, $NO_2$, $Si(R^3)_3$, $B(OR^3)_2$, $OSO_2R^3$, OH, $COOR^3$, $CON(R^3)_2$, a straight-chain alkyl group having 1 to 4 C atoms or a branched or cyclic alkyl group having 3 to 40 C atoms or an alkenyl or alkynyl group having 2 to 40 C atoms, wherein one or more methylene groups in the alkyl, alkenyl and alkynyl groups are optionally replaced by $Si(R^3)_2$, C=O, C=S, C=Se, $C=NR^3$, $P(=O)(R^3)$, SO, $SO_2$, $NR^3$, —O—, —S—, —COO— or —$CONR^3$— and the above-mentioned alkyl, alkenyl and alkynyl groups are optionally substituted by one or more groups $R^3$, or an aromatic ring system having 6 to 60 aromatic ring atoms or heteroaromatic ring system having 5 to 60 aromatic ring atoms, which in each case is optionally substituted by one or more non-aromatic radicals $R^3$, or an aryloxy or heteroaryloxy group having 5 to 60 aromatic ring atoms, which is optionally substituted by one or more non-aromatic radicals $R^3$, or a combination of these systems, wherein two radicals R optionally define an aliphatic or aromatic ring system;
$R^1$ is, identically or differently on each occurrence, a straight-chain alkyl group having 1 to 8 C atoms or a branched or cyclic alkyl group having 3 to 8 C;
$R^2$ is, identically or differently on each occurrence, H, D, F, Cl, Br, I, CHO, $N(Ar)_2$, $N(R^3)_2$, $C(=O)R^3$, $P(=O)(R^3)_2$, $S(=O)R^3$, $S(=O)_2R^3$, $CR^3=C(R^3)_2$, CN, $NO_2$, $Si(R^3)_3$, $B(OR^3)_2$, $OSO_2R^3$, OH, $COOR^3$, $CON(R^3)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^3$, wherein one or more non-adjacent methylene groups are optionally replaced by $Si(R^3)_2$, C=O, C=S, C=Se, $C=NR^3$, $P(=O)(R^3)$, SO, $SO_2$, $NR^3$, —O—, —S—, —COO— or —$CONR^3$— and wherein one or more H atoms are optionally replaced by D, F, Cl, Br, I, CN or $NO_2$, or an aromatic ring system having 6 to 60 aromatic ring atoms or heteroaromatic ring system having 5 to 60 aromatic ring atoms, which in each case is optionally substituted by one or more non-aromatic radicals $R^3$, or an aryloxy or heteroaryloxy group having 5 to 60 aromatic ring atoms, which is optionally substituted by one or more non-aromatic radicals $R^3$, or a combination of these systems, wherein two or more radicals $R^2$ optionally define an aliphatic or aromatic ring system;
$R^3$ is, identically or differently on each occurrence, H, D, F, Cl, Br, I, CHO, $N(R^4)_2$, $C(=O)R^4$, $P(=O)(R^4)_2$, $S(=O)R^4$, $S(=O)_2R^4$, $CR^4=C(R^4)_2$, CN, $NO_2$, $Si(R^4)_3$, $B(OR^4)_2$, $OSO_2R^4$, OH, $COOR^4$, $CON(R^4)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^4$, wherein one or more non-adjacent methylene groups are optionally replaced by $Si(R^4)_2$, C=S, C=Se, C—$NR^4$, $P(=O)(R^4)$, SO, $SO_2$, $NR^4$, —O—, —S—, —COO— or —$CONR^4$— and wherein one or more H atoms are optionally replaced by D, F, Cl, Br, I, CN or $NO_2$, or an aromatic ring system having 6 to 60 aromatic ring atoms or heteroaromatic ring system having 5 to 60 aromatic ring atoms, which in each case is optionally substituted by one or more non-aromatic radicals $R^4$, or an aryloxy or heteroaryloxy group having 5 to 60 aromatic ring atoms, which is optionally substituted by one or more non-aromatic radicals $R^4$, or a combination of these systems, wherein two or more radicals $R^3$ optionally define an aliphatic or aromatic ring system;

$R^4$ is, identically or differently on each occurrence, H, D, F or an aliphatic, aromatic, and/or heteroaromatic organic radical having 1 to 20 C atoms, wherein one or more H atoms are optionally replaced by D or F; and wherein two or more identical or different substituents $R^4$ optionally define an aliphatic or aromatic ring system;

Ar is, identically or differently on each occurrence, an aryl or heteroaryl group having 5 to 60 aromatic C atoms, and optionally substituted by one or more radicals $R^3$;

n is, identically or differently on each occurrence, 0 or 1, wherein when n=0 the group Y in question is not present.

2. The electroluminescent device of claim 1, wherein 2 to 4× per aromatic six-membered ring is $CR^1$.

3. The electroluminescent device of claim 1, wherein said compound is a compound of formula (II)

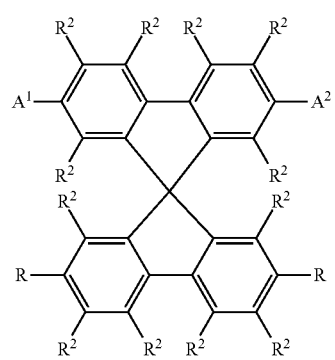

formula (II)

wherein $A^1$ and $A^2$ are selected, identically or differently on each occurrence, from the group consisting of formulae (1-35) to (1-55):

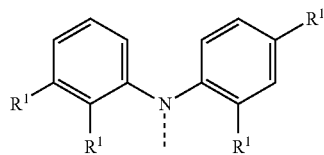

formula (1-36)

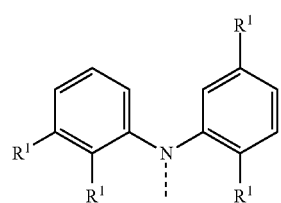

formula (1-37)

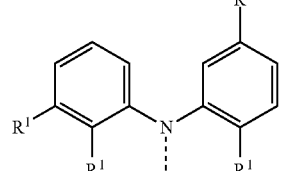

formula (1-38)

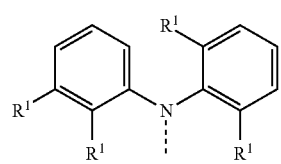

formula (1-39)

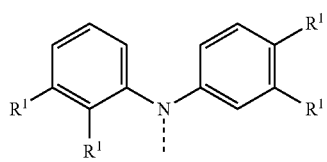

formula (1-40)

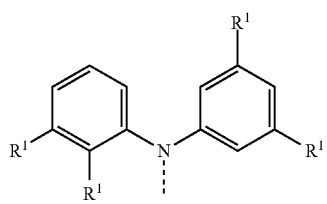

formula (1-41)

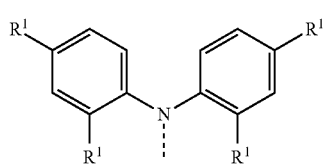

formula (1-42)

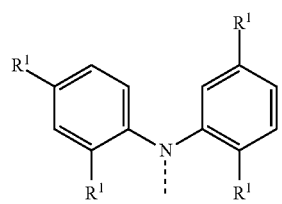

formula (1-43)

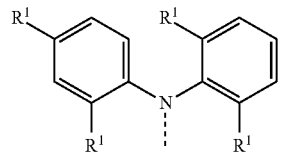

formula (1-44)

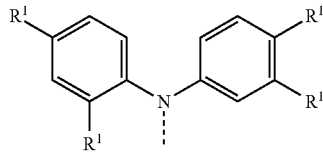

formula (1-45)

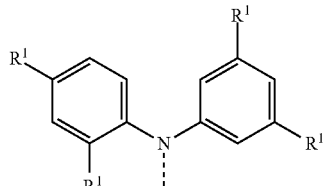

formula (1-46)

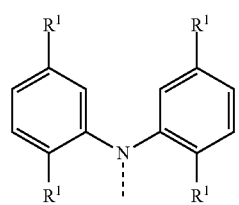

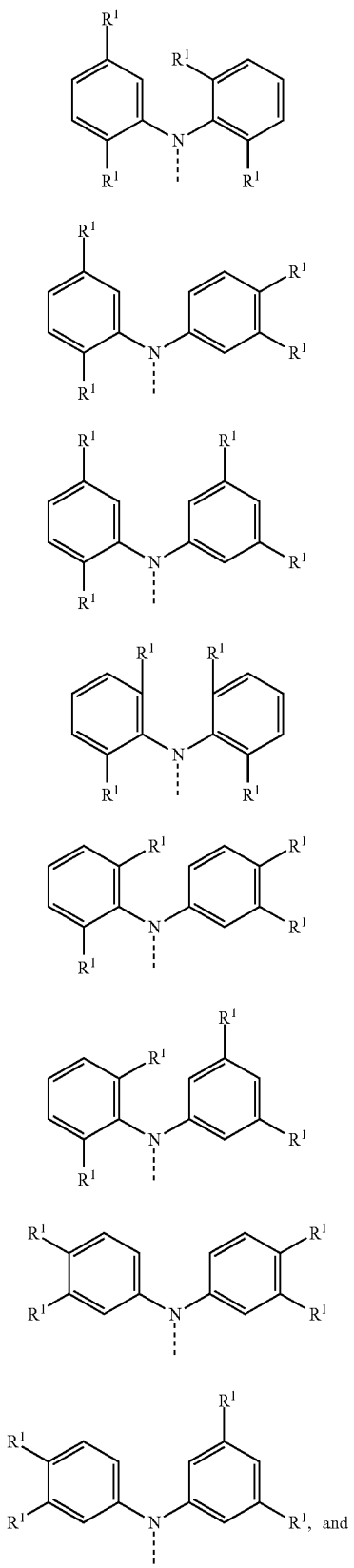

wherein the dashed line represents the bond from the group to the spirobifluorene unit of the compound of formula (II).

4. The electroluminescent device of claim 3, wherein $A^1$ and $A^2$ are identical.

5. The electroluminescent device of claim 1, wherein R is, identically or differently on each occurrence, selected from the group consisting of H, D, an aromatic ring system having 6 to 14 aromatic ring atoms, and a heteroaromatic ring system having 5 to 14 aromatic ring atoms, optionally substituted by one or more non-aromatic radicals $R^3$.

6. The electroluminescent device of claim 1, wherein $R^1$ is selected from methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl or 2-ethylhexyl.

7. The electroluminescent device of claim 1, wherein the hole-transport material, the matrix material, or the emitter material is prepared with a formulation including the at least one compound of formula I and at least one solvent.

8. The electroluminescent device of claim 1, wherein said compound is present in the hole-transport material as a hole-transport layer or a hole-injection layer and/or as a matrix material in the emitting layer.

9. The electroluminescent device of claim 4, wherein $R^2$ is H.

10. The electroluminescent device of claim 4, wherein the groups $A^1$ and $A^2$ are selected from formulae (1-36), (1-39), (1-41), (1-42), (1-43), (1-44), (1-45), (1-48), (1-51), (1-53) or (1-54).

11. The electroluminescent device of claim 5, wherein $R^1$ is selected from methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl or 2-ethylhexyl.

12. The electroluminescent device of claim 3, wherein R is, identically or differently on each occurrence, selected from the group consisting of H, D, an aromatic ring system having 6 to 14 aromatic ring atoms, and a heteroaromatic ring system having 5 to 14 aromatic ring atoms, optionally substituted by one or more non-aromatic radicals $R^3$.

13. The electroluminescent device of claim 3, wherein $R^1$ is selected from methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl or 2-ethylhexyl.

14. The electroluminescent device of claim 12, wherein $R^1$ is selected from methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl or 2-ethylhexyl.

15. The electroluminescent device of claim 1 being an organic electroluminescent device.

16. The electroluminescent device of claim 3 being an organic electroluminescent device.

* * * * *